(12) United States Patent
Tsubota

(10) Patent No.: US 10,660,182 B2
(45) Date of Patent: May 19, 2020

(54) DISPLAY SYSTEM, ELECTRONIC DEVICE, AND LIGHTING SYSTEM

(71) Applicant: TSUBOTA LABORATORY, INC., Tokyo (JP)

(72) Inventor: Kazuo Tsubota, Tokyo (JP)

(73) Assignee: TSUBOTA LABORATORY, INC., Tokyo (JP)

( * ) Notice: Subject to any disclaimer, the term of this patent is extended or adjusted under 35 U.S.C. 154(b) by 0 days.

(21) Appl. No.: 16/473,487

(22) PCT Filed: Dec. 26, 2017

(86) PCT No.: PCT/JP2017/046568
§ 371 (c)(1),
(2) Date: Oct. 2, 2019

(87) PCT Pub. No.: WO2018/124036
PCT Pub. Date: Jul. 5, 2018

(65) Prior Publication Data
US 2020/0092971 A1 Mar. 19, 2020

(30) Foreign Application Priority Data

Dec. 26, 2016 (JP) .................. 2016-250724

(51) Int. Cl.
*H05B 47/10* (2020.01)
*H05B 47/105* (2020.01)
*G06F 3/147* (2006.01)

(52) U.S. Cl.
CPC ........... *H05B 47/105* (2020.01); *G06F 3/147* (2013.01)

(58) Field of Classification Search
CPC ........ H05B 33/08; H05B 37/02; H05B 47/00; H05B 47/105; H05B 47/16; H05B 47/10; H05B 45/10; H05B 45/18; G06F 3/147
See application file for complete search history.

(56) References Cited

U.S. PATENT DOCUMENTS

2014/0285477 A1* 9/2014 Cho .................. G09G 5/02
345/207

FOREIGN PATENT DOCUMENTS

JP     11-237581 A    8/1999
JP    2007-534349 A    11/2007
(Continued)

OTHER PUBLICATIONS

International Search Report in International Application No. PCT/JP2017/046568, dated Feb. 20, 2018.
(Continued)

*Primary Examiner* — Jimmy T Vu
(74) *Attorney, Agent, or Firm* — Sughrue Mion, PLLC

(57) ABSTRACT

To provide a display system such as a smartphone, a game console, a personal computer, or a liquid crystal television, including a light-emitting element that irradiates light having a specific wavelength toward a user. The above-described problem is solved by a display system (1) including a first light-emitting element (6) that emits light used for image display, a second light-emitting element (3) that irradiates light (7) within a wavelength range of 360 nm to 400 nm, inclusive, toward a user, and a control unit (10) that controls irradiation of the light (7) from the second light-emitting element (3). At this time, the second light-emitting element (3) may be a single light-emitting element integrated with the first light-emitting element (6) or a light-emitting element provided separately from the first light-emitting element (6). When separately provided from the first light-emitting element (6), the second light-emitting element (3) is preferably provided to a peripheral frame (4) of a display screen (2), in the display screen (2), or as an accessory (5).

20 Claims, 13 Drawing Sheets

(56) References Cited

FOREIGN PATENT DOCUMENTS

| JP | 3191854 U | 7/2014 |
|----|-----------|--------|
| JP | 2015-177403 A | 10/2015 |
| JP | 2016-76120 A | 5/2016 |
| WO | 2014/155497 A1 | 10/2014 |
| WO | 2015/186723 A1 | 12/2015 |

OTHER PUBLICATIONS

Written Opinion in International Application No. PCT/JP2017/046568, dated Feb. 20, 2018.

Megumi Hatori et al., "Circadian Clock and Eyes", Anti-Aging Medicine—Journal of Japanese Society of Anti-Aging Medicine, Medical Review Co., Ltd., 2015, vol. 11, No. 3, pp. 065(385)-072(392) (17 pages total).

Ian Morgan, "Myopia: The Evidence for Environmental Factors", Environmental Health Perspectives, Jan. 2014, vol. 122, No. 1, pp. A13-A19 (8 pages total).

Lisa A. Jones et al., "Parental History of Myopia, Sports and Outdoor Activities, and Future Myopia", Investigative Ophthalmology & Visual Science, Association for Research in Vision and Ophthalmology, Aug. 2007, vol. 48, No. 8, pp. 3524-3532 (9 pages total).

Per G. Soderberg, "Optical radiation and the eyes with special emphasis on children", Progress in Biophysics and Molecular Biology, 2011, vol. 107, pp. 389-392 (4 pages total).

Takeshi Saito et al., "Protective Effects of Metallothionein I and II against Metal- and Ultraviolet Radiation-Induced Damage in Cultured Lens Epithelial Cells", Japanese Journal Ophthalmological Society, 2010, vol. 54, pp. 486-493 (8 pages total).

Kazuo Tsubota, "Blue Light—Threat to Internal Clock", Shueisha, Nov. 20, 2013 (6 pages total).

Hidemasa Torii et al., "Violet Light Exposure Can Be a Preventive Strategy Against Myopia Progression", EBioMedicine, 2017, vol. 15, pp. 210-219 (10 pages total).

* cited by examiner

DISPLAY SYSTEM, ELECTRONIC DEVICE, AND LIGHTING SYSTEM

CROSS REFERENCE TO RELATED APPLICATIONS

This application is a National Stage of International Application No. PCT/JP2017/046568 filed Dec. 26, 2017, claiming priority based on Japanese Patent Application No. 2016-250724, filed Dec. 26, 2016.

FIELD OF THE INVENTION

The present invention relates to a display system and the like including a light-emitting element for light having a specific wavelength.

BACKGROUND ART

In the living environment, there exists light with various wavelengths. Such light reportedly affects the human body and mind. For example, in Non-Patent Document 1, it is reported that the internal clock is improved by exposure to sunlight, and the like. Further, in Non-Patent Document 2, it is reported that light emitted from light-emitting diode (LED) lighting, a liquid crystal display that uses an LED for a backlight, and the like, which have existed in the living environment in recent years, significantly affects the body and mind.

There have also been several reports on the effects of light on the eyes. For example, in Non-Patent Documents 3 and 4, the eye reportedly sustains various damage when exposed to ultraviolet light. For that reason, many products, such as eyeglasses and contact lenses, that minimize the transmission of ultraviolet light to the extent possible to prevent eye exposure to ultraviolet light that may cause damage are now commercially available.

Further, in Non-Patent Document 5, outdoor activity in sunlight is described as related to the suppression of myopia. Further, in Patent Document 1 and Non-Patent Document 7, it is proposed that light having a specific wavelength is effective in myopia prevention. With the number of persons with myopia continually on the rise worldwide in recent years, means for preventing the occurrence and means for delaying the progression of such myopia are in high demand.

Non-Patent Documents

Non-Patent Document 1: Megumi Hatori, Kazuo Tsubota, Anti-Aging Medicine—Journal of Japanese Society of Anti-Aging Medicine, Vol. 11, No. 3, 065(385)-072(392), (2015)
Non-Patent Document 2: Kazuo Tsubota, "Blue Light— Threat to Internal Clock", Shueisha (Nov. 20, 2013)
Non-Patent Document 3: Saito, et. al., Japanese Journal of Ophthalmology, 54, p. 486-493 (2010)
Non-Patent Document 4: Per G. Soderberg, Progress in Biophysics and Molecular Biology, 107, p. 389-392 (2011)
Non-Patent Document 5: Ian Morgan, Environmental Health Perspectives, Vol. 122, No. 1, January, (2014)
Non-Patent Document 6: Lisa A. Jones, Loraine T. Sinnott, Donald O. Mutti, Gladys L. Mitchell, Melvin L. Moeschberger, and Karla Zadnik, Investigative Ophthalmology & Visual Science, Vol. 48, No. 8, August, (2007)
Non-Patent Document 7: Hidemasa Torii, et al., EBioMedicine, "DOI: http//dx.doi.org/10.1016/j.ebiom.2016.12.007"

Patent Documents

Patent Document 1: WO2015/186723 A1

SUMMARY OF THE INVENTION

Problems to be Solved by the Invention

The present inventors have reported that, as described in Non-Patent Documents 1 and 2, light affects the body and mind. In the past, exposure to light was simply sunlight outdoors and the light of lighting indoors.

Nevertheless, recently, with the spread of LED lighting and display devices such as smartphones, game consoles, personal computers, and liquid crystal televisions, there is concern that the living environment and the work environment have changed, that the wavelengths of light to which a person is exposed are now specific (limited), and that such conditions may have various effects on the body and mind. This may lead to various problems that have never occurred to date.

Further, as described in Patent Document 1 and Non-Patent Document 7, the present inventors, in the process of researching the suppression of the onset and the progression of myopia, discovered that allowing sunlight to enter the eyes is effective in suppressing the onset and the progression of myopia, and irradiating light having, among the wide range of wavelengths included in sunlight, a wavelength range of 360 nm to 400 nm, inclusive, on the eyeball may suppress the onset and the progression of myopia, and have been proposed a novel myopia preventing article (refer to Patent Document 1).

Nevertheless, with smartphones and the like, light for displaying images (including moving images; abbreviated as image display light) is continually irradiated during use, and therefore this image display light must be considered.

The present invention has been made to solve the problems described above, and an object of the present invention is to provide, in a display system including a light-emitting element for image display that emits light used for image display, a display system or the like capable of irradiating light having a specific wavelength, which is missing in a modern lifestyle, toward the eyes of the user, suppressing adverse effects caused by various light, and imparting a favorable effect on the body.

Means for Solving the Problems

A display system according to the present invention is configured to include a first light-emitting element that emits display light used for image display, a second light-emitting element that irradiates a first special light within a wavelength range of 360 nm to 400 nm, inclusive, toward the user, and a control unit that controls irradiation of the first special light from the second light-emitting element.

With this configuration, it is possible to irradiate light having the above-described specific wavelength, which is missing in a modern lifestyle, toward the eyes of the user, and thus promote a favorable effect of eye exposure to the light such as, for example, the suppression of the onset and the progression of myopia. Further, depending on a usage environment capable of intentionally restricting and irradiating, among the display light emitted from the first light-emitting element, light having the applicable specific wavelength toward the eyes of the user, it is possible to control the light emitted from the first light-emitting element and suppress adverse effects that may occur due to eye exposure to light.

Effect of the Invention

According to the present invention, it is possible to provide a display system and the like capable of irradiating light having a specific wavelength, which is missing in a modern lifestyle, toward the eyes of a user, suppressing adverse effects caused by various light, and imparting a favorable effect on the body.

Figure 1:
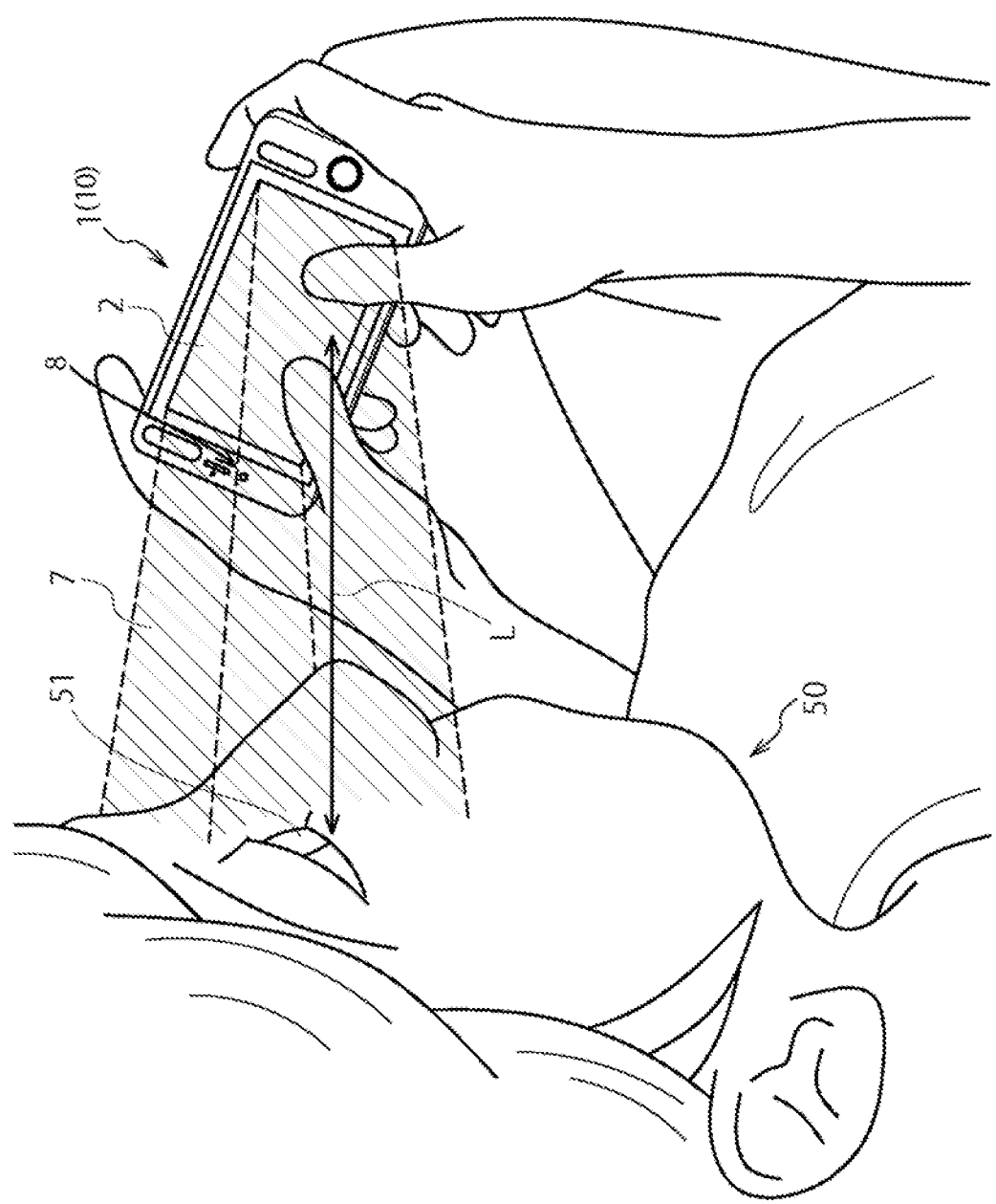
FIG. 1 is an example in which a first light-emitting element and a second light-emitting element are provided in a display screen of a smartphone in a first embodiment of the present application.

EMBODIMENTS OF THE INVENTION (1) A display system according to the present invention is configured to include a first light-emitting element that emits display light used for image display, a second light-emitting element that irradiates a first special light within a wavelength range of 360 nm to 400 nm, inclusive, toward the user, and a control unit that controls irradiation of the first special light from the second light-emitting element.

With this configuration, it is possible to irradiate light having the above-described specific wavelength, which is missing in a modern lifestyle, toward the eyes of the user, and thus promote a favorable effect of eye exposure to the light such as, for example, the suppression of the onset and the progression of myopia. Further, the present invention is capable of intentionally restricting and irradiating, among the display light emitted from the first light-emitting element, light having the applicable specific wavelength toward the eyes of the user. Further, the present invention is capable of controlling the light emitted from the first light-emitting element in accordance with the usage environment, and suppressing adverse effects that may occur due to eye exposure to light.

(2) In the display system according to the present invention, the second light-emitting element is configured to be a single light-emitting element integrated with the first light-emitting element or a light-emitting element provided separately from the first light-emitting element.

(3) In the display system according to the present invention, the second light-emitting element is configured to be (A) provided to a peripheral frame of a display screen, (B) provided in a display screen, or (C) provided as an accessory, when separately provided from the first light-emitting element.

With this configuration, it is possible to provide the second light-emitting element to the display device by various forms.

(4) The display system according to the present invention is configured to further include detecting means for detecting at least one of (A) a position of an eye of the user, (B) an open/closed state of an eyelid, (C) a distance to the eye, and (D) a line-of-sight direction of the user. The control unit controls irradiation of the first special light to the eye of the user on the basis of at least one of the position of the eye, the open/closed state of the eyelid, the distance to the eye, and the line-of-sight direction of the user detected by the detecting means.

With this configuration, it is possible to appropriately irradiate light within a wavelength range of 360 nm to 400 nm, inclusive, onto the eyes. It should be noted that examples of a control unit include a direction variable device that allows variation of the irradiation direction of the second light-emitting element and the like.

(5) In the display system according to the present invention, the control unit is configured to cause the second light-emitting element to irradiate the first special light when the line of sight of the user is determined to be toward a display screen displaying the image on the basis of the detected line-of-sight direction.

With this configuration, it is possible to reliably irradiate the first special light onto the eyes of the user and prevent wasteful irradiation of the first special light in a state in which the user is not viewing the display image, and thus achieve power saving.

(6) In the display system according to the present invention, the control unit is configured to set at least one control item of an irradiation time, an irradiation period, and an irradiance of the first special light emitted from the second light-emitting element, and control irradiation of the first special light on the basis of the set control item.

With this configuration, it is possible to set the irradiation time and irradiance of the light emitted from the second light-emitting element by a time unit or the like, and thus irradiate light having a specific wavelength onto the eyes for an arbitrary time and at arbitrary intensity in accordance with a mode of use of each user.

(7) The display system according to the present invention is configured to further include a first optical sensor that measures a state of the first special light at a position of the eye of the user. The control unit controls irradiation of the first special light emitted from the second light-emitting element in accordance with a measurement result of the first optical sensor.

With this configuration, it is possible to measure the state of the light at the position of the eyes using an optical sensor and, because output of the light emitted from the second light-emitting element is controlled in accordance with the measurement result, output light corresponding to the usage environment without setting the light by, for example, a time unit, a day unit, or the like.

(8) The display system according to the present invention is configured to further include a second optical sensor that measures a state of light at a position of the eye of the user in the environment in which the user is placed. The control unit controls irradiation of the first special light emitted from the second light-emitting element in accordance with a measurement result of the second optical sensor, and adjusts output of the display light emitted from the first light-emitting element in accordance with the first special light emitted from the second light-emitting element.

With this configuration, it is possible to irradiate light preferred in the usage environment onto the user by the first special light, the light of the surrounding environment of the user (such as sunlight or the light irradiated from a lighting fixture, for example), and the display light.

(9) In the display system according to the present invention, the control unit is configured to control irradiation of the first special light emitted from the second light-emitting element in accordance with the measurement result of the first optical sensor, and adjust output of the display light emitted from the first light-emitting element in accordance with the first special light emitted from the second light-emitting element.

With this configuration, because output of the light emitted from the second light-emitting element is controlled in accordance with the first special light, it is possible to output light corresponding to the usage environment without setting the light by, for example, a time unit, a day unit, or the like.

(10) The display system according to the present invention is configured to further include management means for acquiring irradiation data related to at least one control item of an irradiation time, an irradiation period, and an irradiance of the first special light irradiated from the second light-emitting element, and storing the acquired irradiation data in first storage means so as to allow use in a predetermined activity of the user.

With this configuration, it is possible to manage the irradiation history of the user, and thus associate the irradiation history with, for example, a predetermined user activity such as eye test results or life rhythm management and, as a result, improve user-friendliness in relation to user activities.

(11) In the display system according to the present invention, the management means is configured to acquire measurement data indicating a measurement result of the first special light measured at a position of the eye of the user, store the acquired irradiation data and the measurement data in association with a time in the first storage means, and supply the stored irradiation data and measurement data to an external device.

With this configuration, it is possible to manage the data of the first special light emitted from the second light-emitting element in accordance with the usage environment.

(12) In the display system according to the present invention, the control unit is configured to acquire at least data indicating a given activity of the user within a predetermined past period as personal data, and control the irradiation of the first special light from the second light-emitting element on the basis of the acquired personal data.

With this configuration, it is possible to, for example, calculate an insufficiency in an energy amount of sunlight to which the user was exposed in the past 24 hours, provide compensation for the insufficiency to the user, and cause the second light-emitting element to accurately emit light in accordance with the required energy amount.

(13) The display system according to the present invention is configured to further include second recording means with the personal data recorded thereon. The control unit acquires the personal data from the second recording means.

With this configuration, it is possible to execute various processing by using the prerecorded personal data, and thus increase processing speed.

(14) In the display system according to the present invention, the control unit is configured to acquire weather information indicating the weather in a time band during the day, specify a period when the user was outdoors in a time band during the day for a predetermined past period as an outdoor location period on the basis of the acquired personal data, and control irradiation of the first special light from the second light-emitting element on the basis of the specified outdoor location period and the acquired weather information.

With this configuration, it is possible to control output of the first special light in accordance with the weather of a location of the user, and thus reliably irradiate the first special light in a required energy amount onto the eyes of the user with high precision, even when the irradiance of sunlight that reaches the ground changes due to the weather.

(15) In the display system according to the present invention, the control unit is configured to acquire an average value of spectral irradiance for outdoor measurement of the first special light for each weather type in advance, calculate an energy amount of the first special light irradiated onto the eyes of the user during the day on the basis of the acquired average value, the specified outdoor location period, and the acquired weather information, determine an illuminance and an irradiation period of the first special light irradiated from the second light-emitting element on the basis of the calculated energy amount and an ideal irradiated energy amount acquired in advance, and irradiate the first special light from the second light-emitting element on the basis of the determined illuminance and irradiation period.

With this configuration, it is possible to irradiate an insufficiency onto the eyes of the user by the second light-emitting element while specifying with high precision an energy amount of the first special light included in sunlight to which the user was exposed during outdoor activity.

(16) In the display system according to the present invention, an irradiance of light emitted from the second light-emitting element is configured to be 10 W/m$^2$ or less.

With this configuration, it is possible to delay the onset or suppress the progression of myopia.

(17) The display system according to the present invention is configured to further include a third light-emitting element that irradiates a second special light within a wavelength range of 460 nm±20 nm toward the user, and control irradiation of the second special light from the third light-emitting element.

With this configuration, it is possible to irradiate the second special light within a predetermined wavelength range in accordance with the environment, and thus particularly regulate a circadian rhythm and achieve effects such as regulation, adjustment, prevention, and treatment in relation to the body and mind of the user.

(18) In the display system according to the present invention, the third light-emitting element is configured to be included in the first light-emitting element.

With this configuration, it is possible to irradiate light onto the user at a controlled irradiance while using the third light-emitting element for image display. It should be noted that, as in the preceding paragraph, the third light-emitting element may be provided as an independent light-emitting element.

(19) In the display system according to the present invention, an irradiance of the second special light emitted from the third light-emitting element is configured to be 1 $W/m^2$ or less.

With this configuration, it is possible to regulate the circadian rhythm.

(20) In the display system according to the present invention, at least one or both of light within a range of 435 nm±10 nm and light within a range of 505 nm±10 nm is configured to be restricted.

With this configuration, it is possible to restrict light around 430 nm and around 505 nm, to which the retina is highly sensitive, by the control unit.

(21) An electronic device according to the present invention includes a smartphone, a game console, a personal computer, a liquid crystal television, smart glasses, or other display system having any of the configurations described above.

With this configuration, it is possible to irradiate light having the above-described specific wavelength, which is missing in a modern lifestyle, toward the eyes of the user by various electronic devices, and thus promote a favorable effect of eye exposure to the light such as, for example, the suppression of the onset and the progression of myopia.

(22) A lighting system according to the present invention is configured to include a light source configured by a light-emitting element that irradiates a first special light within a wavelength range of 360 nm to 400 nm, inclusive, and a fluorescent material that covers a periphery of the light-emitting element, and a control unit that controls the light source. The control unit acquires personal data indicating data of a given activity of a user, and controls irradiation of the first special light from the light-emitting element on the basis of the acquired personal data.

With this configuration, it is possible to irradiate light having the above-described specific wavelength, which is missing in a modern lifestyle, toward the eyes of the user by a fixture such as a lighting device, for example, and thus promote a favorable effect of eye exposure to the light such as, for example, the suppression of the onset and the progression of myopia.

Further, depending on a usage environment capable of intentionally restricting and irradiating, among the display light emitted from the first light-emitting element, light having an applicable specific wavelength toward the eyes of the user, the present invention can control the light emitted from the first light-emitting element and suppress adverse effects that may occur due to eye exposure to light.

Embodiments of the present invention are described below. It should be noted that the embodiments described below do not unduly limit the contents of the present invention described in the claims. Further, not all configurations described in the following embodiments are necessarily essential requirements of the present invention.

[1] First Embodiment

[1.1] Overview and Principle

A first embodiment of a display device of the present application will now be described using FIG. 1 to FIG. 6.

Figure 2:
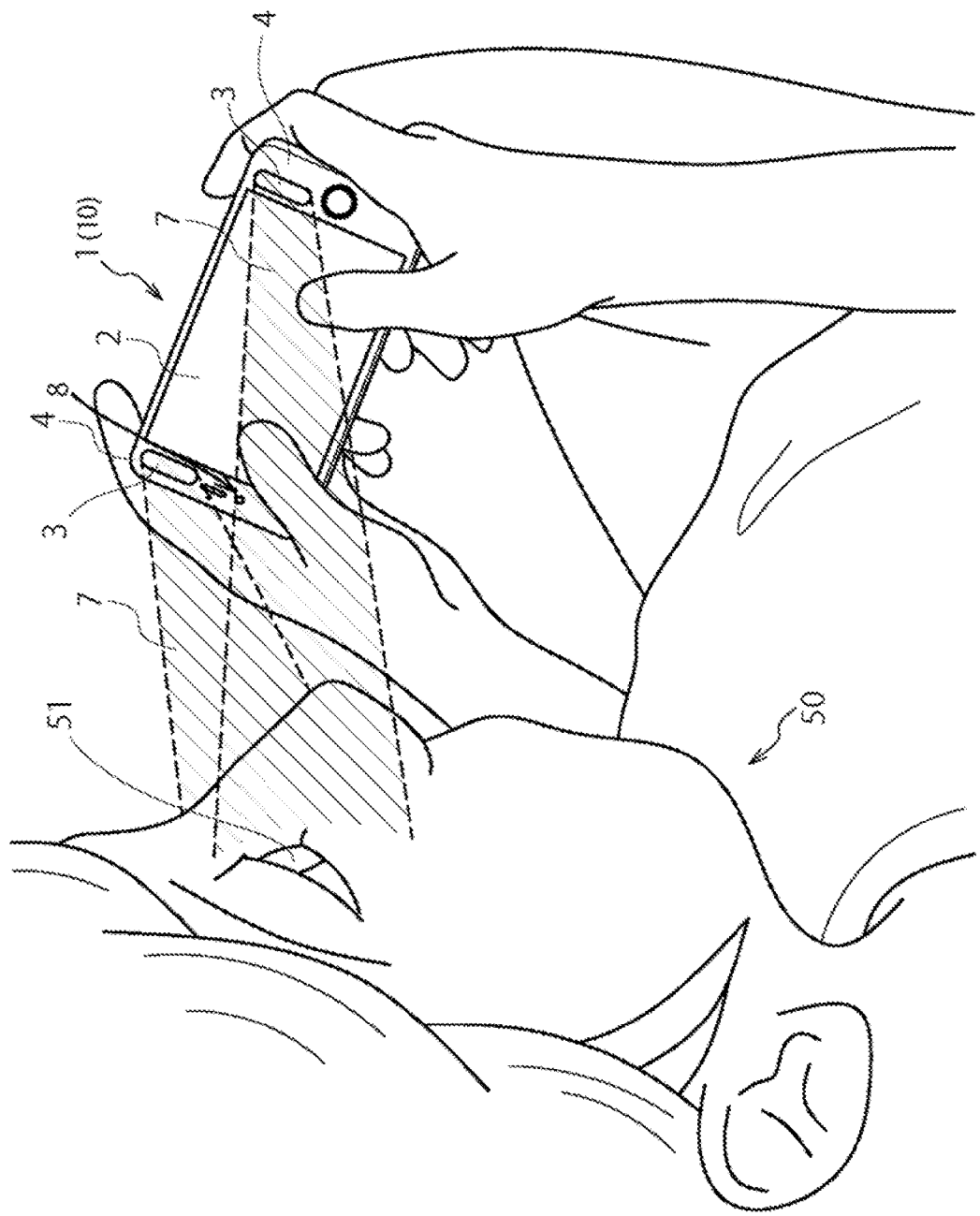
FIG. 2 is an example of the second light-emitting element provided to a frame of the smartphone in the first embodiment.
Figure 3:
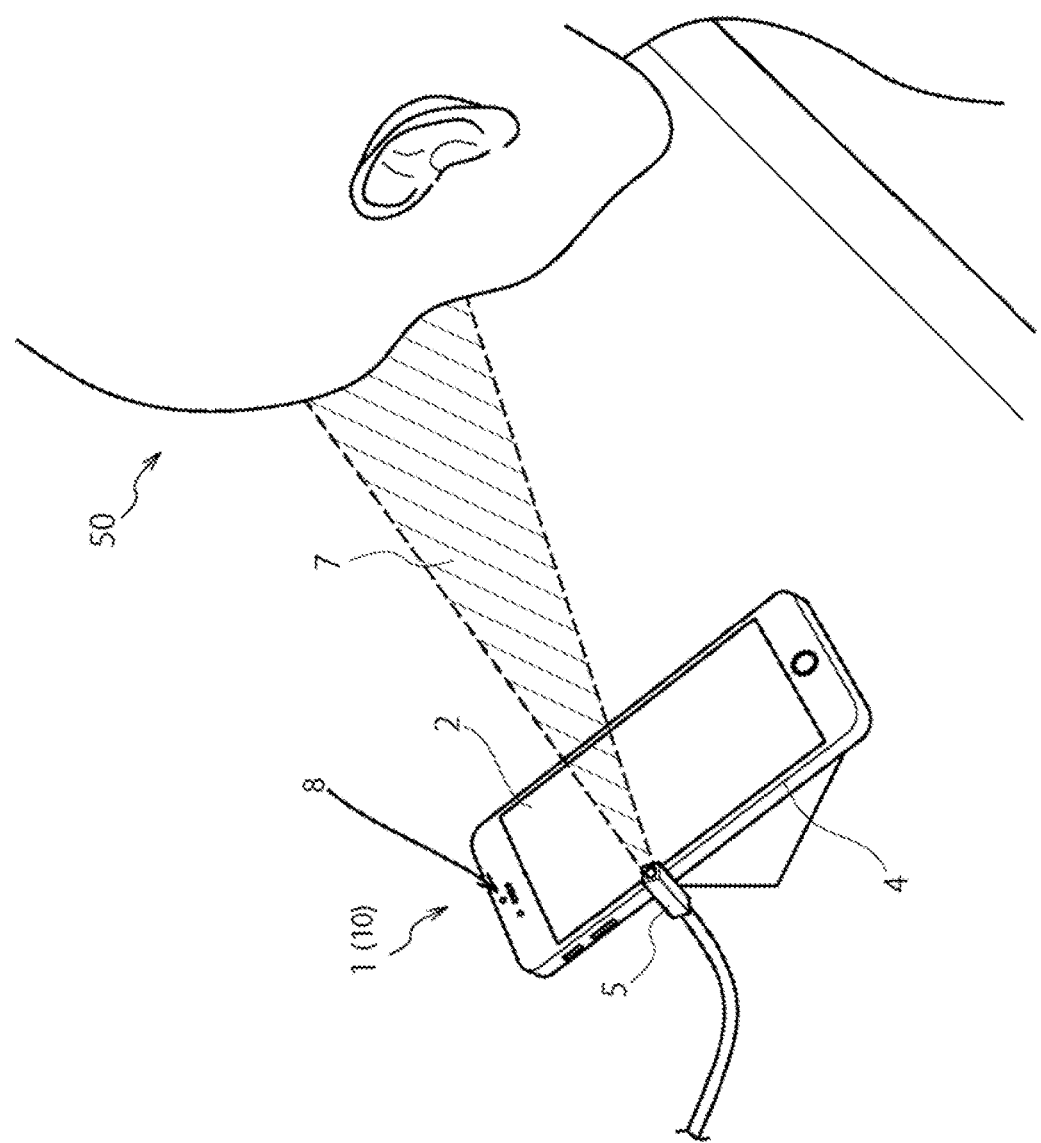
FIG. 3 is an example in which the second light-emitting element is attached as an accessory to the frame of the smartphone in the first embodiment.
Figure 4:
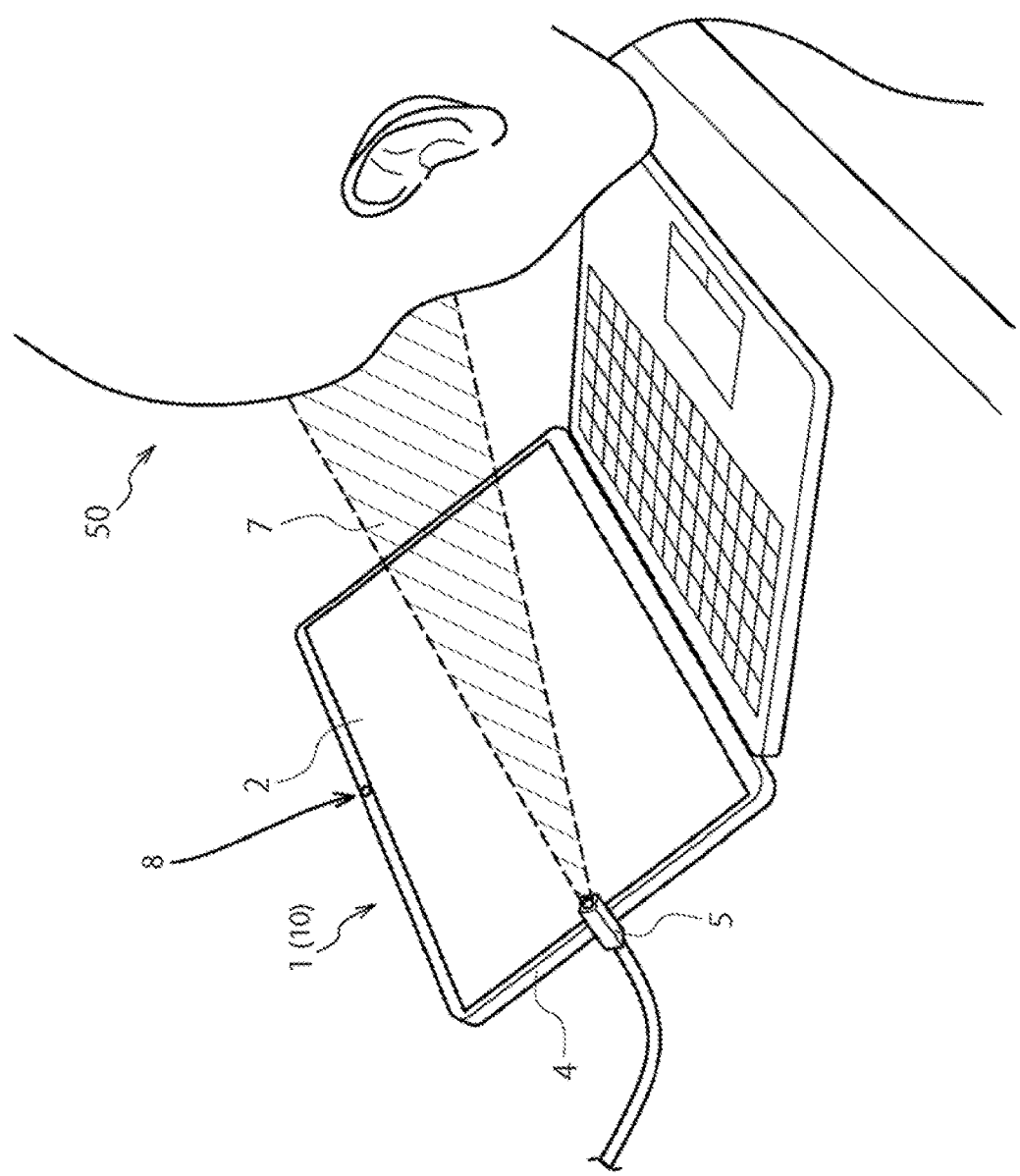
FIG. 4 is an example in which the second light-emitting element is attached as an accessory to a frame of a personal computer in the first embodiment.
Figure 5:
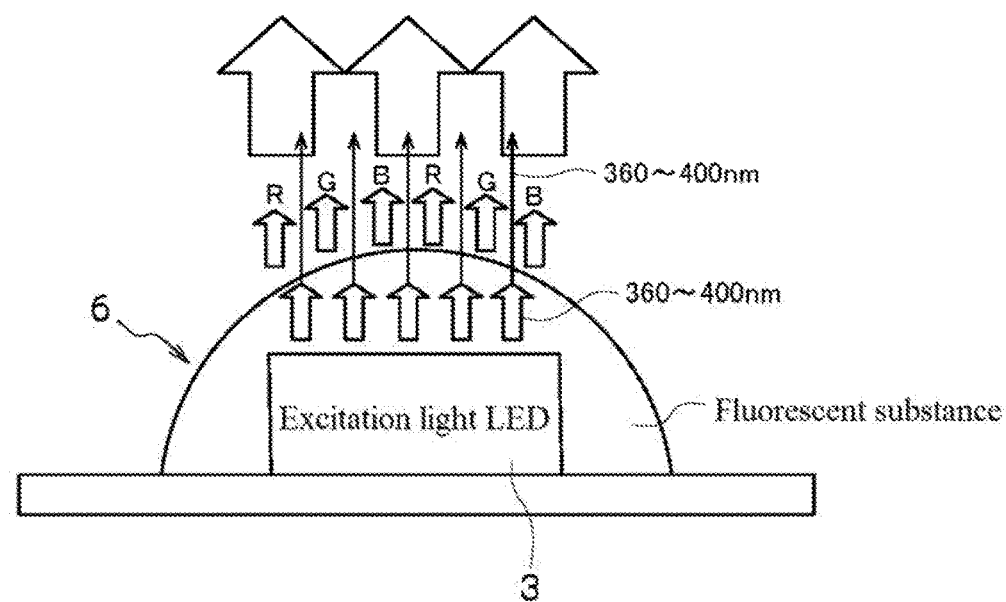
FIG. 5 is an example of a mode in which the first light-emitting element and the second light-emitting element are integrated in the first embodiment.
Figure 6:
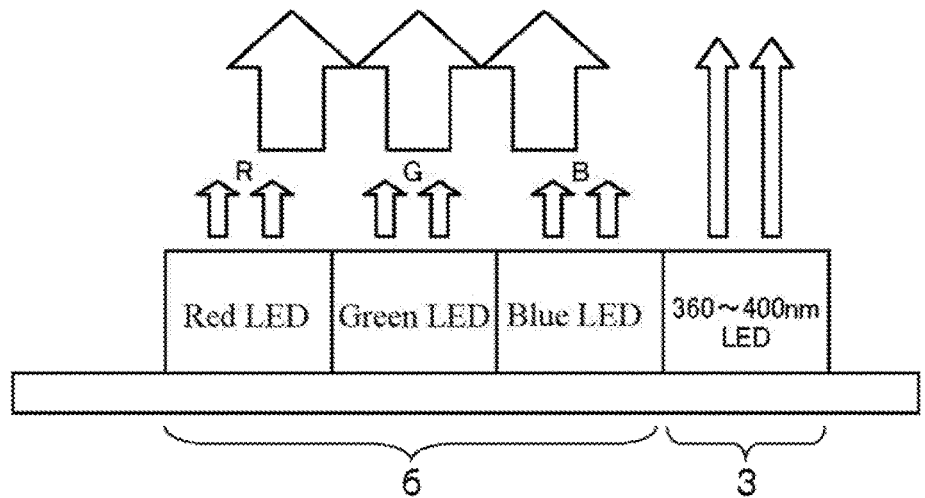
FIG. 6 is another example of a mode in which the first light-emitting element and the second light-emitting element are integrated in the first embodiment.

FIG. 1 is an example in which a first light-emitting element and a second light-emitting element are provided in display screen of a smartphone, and FIG. 2 is an example of the second light-emitting element provided to a frame of the smartphone. FIG. 3 is an example in which the second light-emitting element is attached as an accessory to the frame of the smartphone, and FIG. 4 is an example in which the second light-emitting element is attached as an accessory to a frame of a personal computer. FIG. 5 is an example of a mode in which the first light-emitting element and the second light-emitting element are integrated, FIG. 6 is another example of a mode in which the first light-emitting element and the second light-emitting element are integrated.

A display device 1 of this embodiment is, for example, the display device 1 including a first light-emitting element 6 that emits light used for image display, as illustrated in FIG. 1 to FIG. 6. In particular, the display device 1 includes the first light-emitting element 6 that emits light used for image display, a second light-emitting element 3 that irradiates light 7 within a wavelength range of 360 nm to 400 nm, inclusive, toward a user 50, and a control unit 10 that controls irradiation of the light 7 from the second light-emitting element 3.

The display device 1 includes the first light-emitting element 6 that emits light used for general image display, the second light-emitting element 3 that irradiates the light 7 within the above-described wavelength range toward the user 50, and the control unit 10 that controls irradiation of the light 7 from the second light-emitting element 3, making it possible to irradiate the light 7 within the above-described wavelength range onto the user 50.

In modern society, the living environment and the work environment have changed as a result of the dramatic spread of information communication terminal devices such as the smartphone. People spend a great amount of time in their daily lives viewing and working while facing display devices such as smartphones, game consoles, personal computers, and televisions. These information communication terminal devices and display devices are now used for a long period of time across a wide range of ages, from children to the elderly, and may cause various problems that have not occurred up until now. For example, the eye detects a color by a pyramidal cell, which is a type of photoreceptor in the retina, and recognizes movement and the like of an object by its temporal change.

The display device 1 of this embodiment, by irradiating light having a specific wavelength toward the eyes of the user, can promote a favorable effect of eye exposure to the light such as, for example, the suppression of the onset and the progression of myopia. In particular, the display device 1 is effective in solving problems that may occur in modern society in which the living environment and the work environment have changed as a result of the dramatic spread of smartphones and the like, such as the problem of the onset and progression of myopia, for example. Furthermore, the display device 1 makes it possible to achieve effects such as regulation, adjustment, prevention, and treatment in relation to the body and mind of the user 50.

For example, taking into consideration modern living situation in which a smartphone or the like is used mainly indoors over a long period of time, the onset and the progression of myopia can be suppressed by irradiating the light (abbreviated as violet light or VL) 7 of 360 nm to 400 nm, inclusive, toward an eye 51 when necessary. Although such VL 7 is included in sunlight, modern people who are surrounded by various products having ultraviolet (UV) protection and UV cutting functions lack the VL 7. Then, children in recent years spend a shorter amount of time playing outdoors year by year. Therefore, by irradiating the VL 7 toward the eye 51 in accordance with the light environment in which the user 50 lives, it is possible to suppress the onset and the progression of myopia.

The eye 51 not only perceives color but also performs non-visual tasks. For example, melanopsin-containing retinal ganglion cells (mRGC) are known to act most strongly with light having a wavelength within a range of 460 nm±20 nm and affect the circadian rhythm.

Furthermore, for example, specific light included in sunlight regulates the internal clock of a person, but when light having such a specific wavelength is emitted indefinitely from a light-emitting element such as a smartphone, exposure continues indoors as well as during the night. For that reason, the possibility exists that the internal clock will be disrupted, significantly affecting the body and mind of a person. Therefore, if it is possible to irradiate such light (abbreviated as blue light or BL) including 460 nm as within the range of 460 nm±20 nm onto the eyes at a time when the sun should be out during the day, the circadian rhythm can be regulated without disruption.

The display device 1 of this embodiment makes it possible to irradiate the VL 7 having a specific wavelength and capable of achieving effects such as regulation, adjustment, prevention, and treatment in relation to the body and mind of the user 50 toward the eye 51 of the user 50. It should be noted that "circadian rhythm (also referred to as internal clock)" is a physiological phenomenon that fluctuates in an approximate 24-hour cycle and, by allowing BL to enter the eye mainly outdoors during the day, becomes stabilized, thereby stabilizing the appetite, drowsiness, sleep, and the like, eliminating stress as well, and maintaining physical health.

[1.2] Configuration

Figure 9:
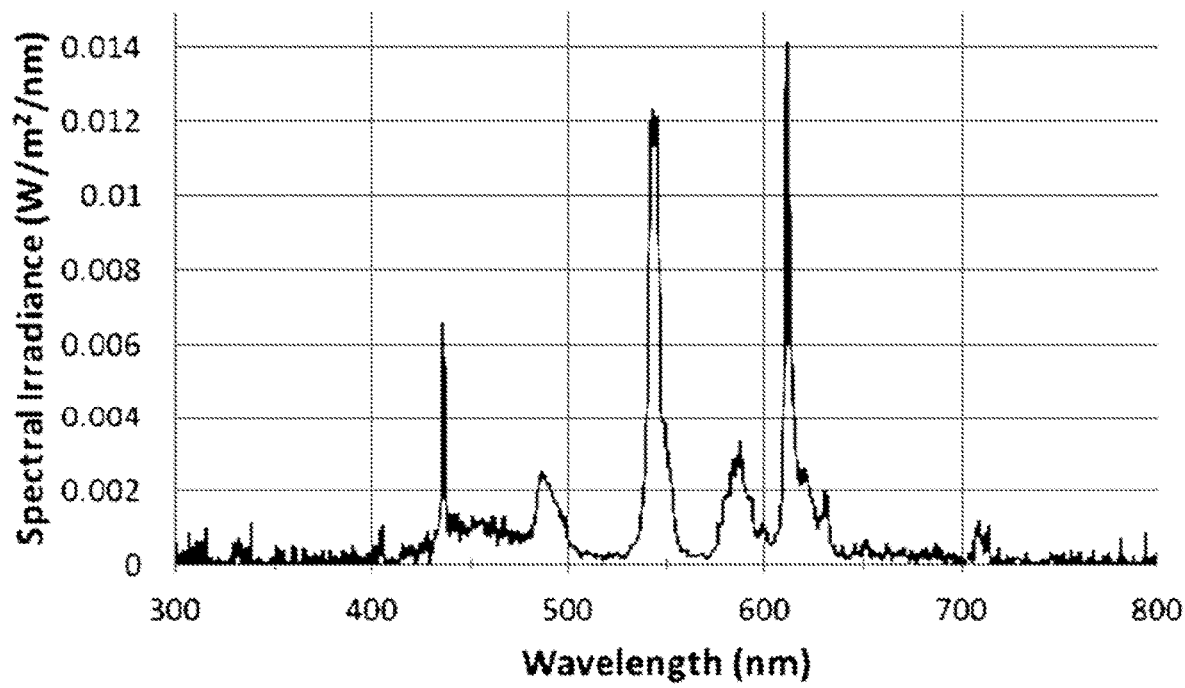
FIG. 9 is an example of a spectrum of light measured in an indoor environment irradiated with a fluorescent lamp.
Figure 10:
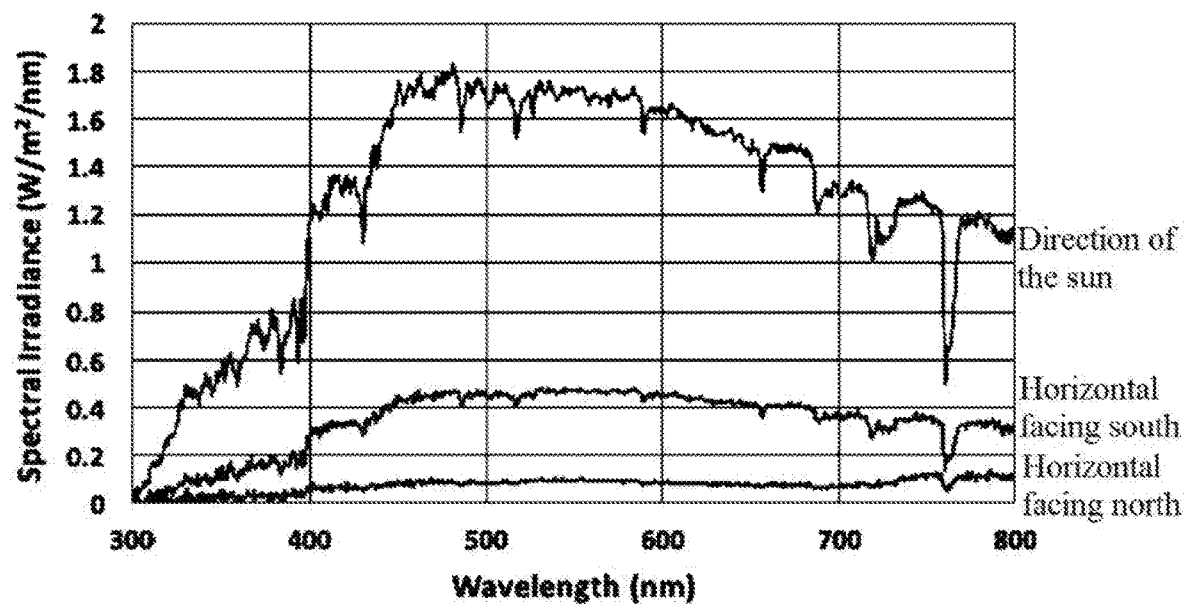
FIG. 10 is an example of a spectrum of light measured in an outdoor environment during the day.
Figure 11:
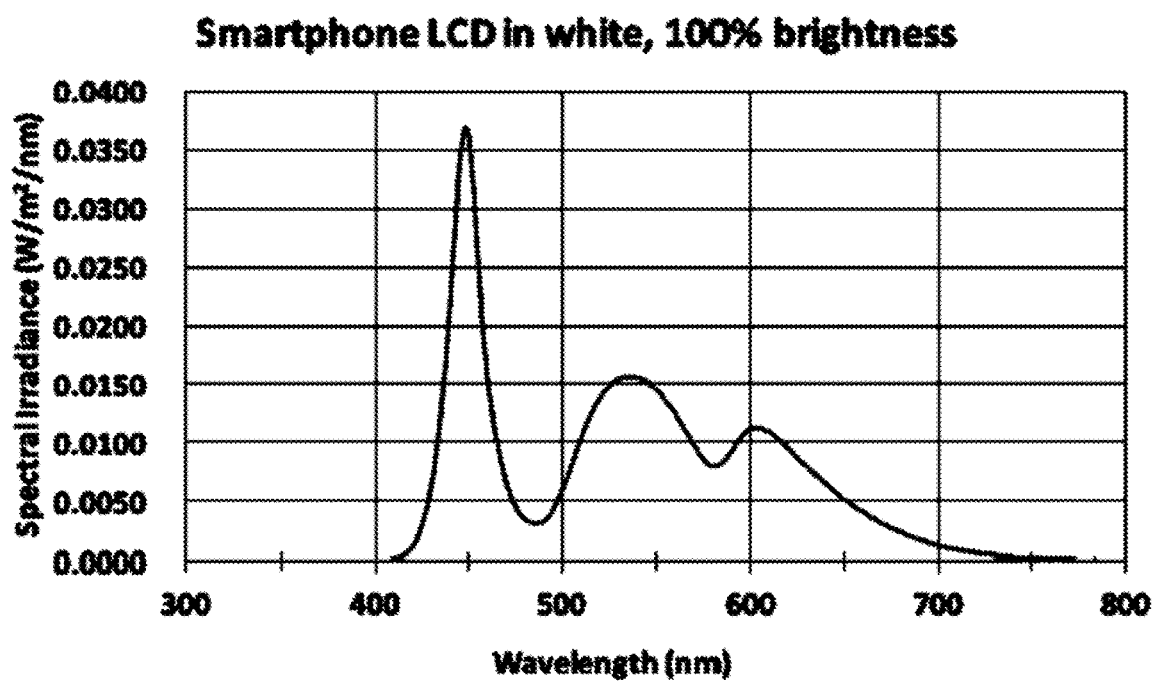
FIG. 11 is an example of a spectrum of light emitted from a smartphone.
Figure 12A:
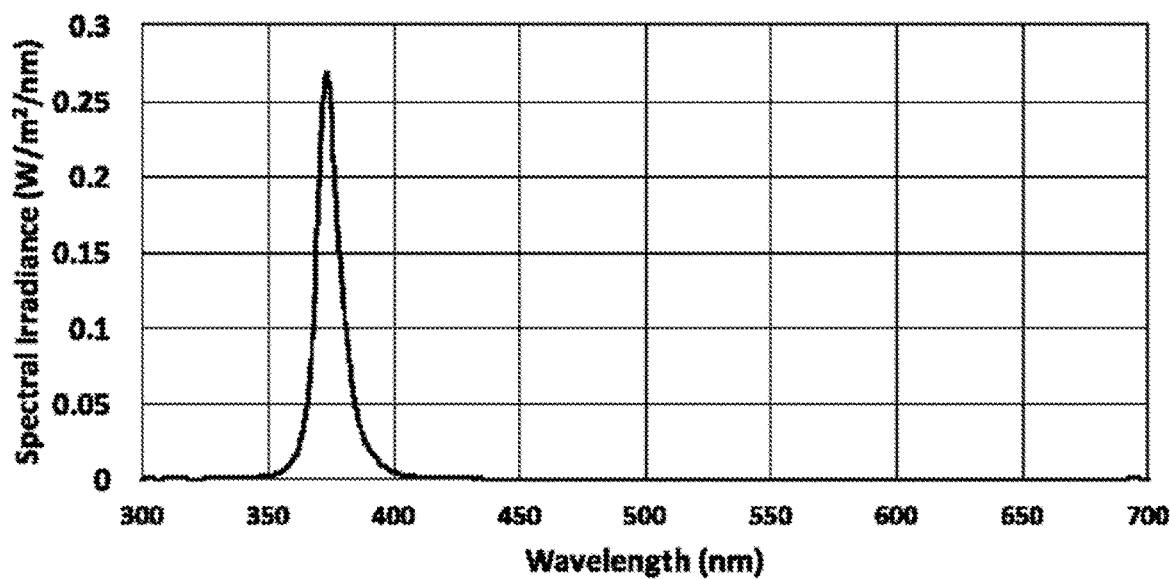
FIG. 12A is an example of a spectrum of light emitted from a display device of the first embodiment, and is a spectrum of light within a range of 360 nm to 400 nm, inclusive.
Figure 12B:
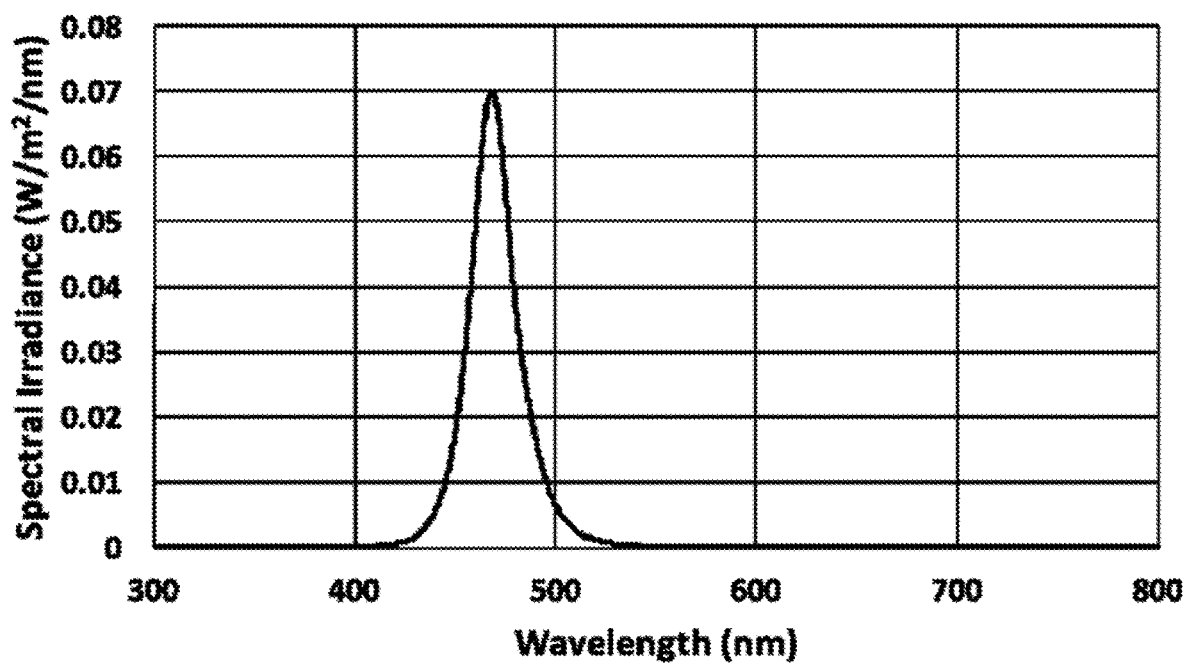
FIG. 12B is an example of a spectrum of light emitted from the display device of the first embodiment, and is an example of a spectrum of light within a range of 460 nm±20 nm.
Figure 13:
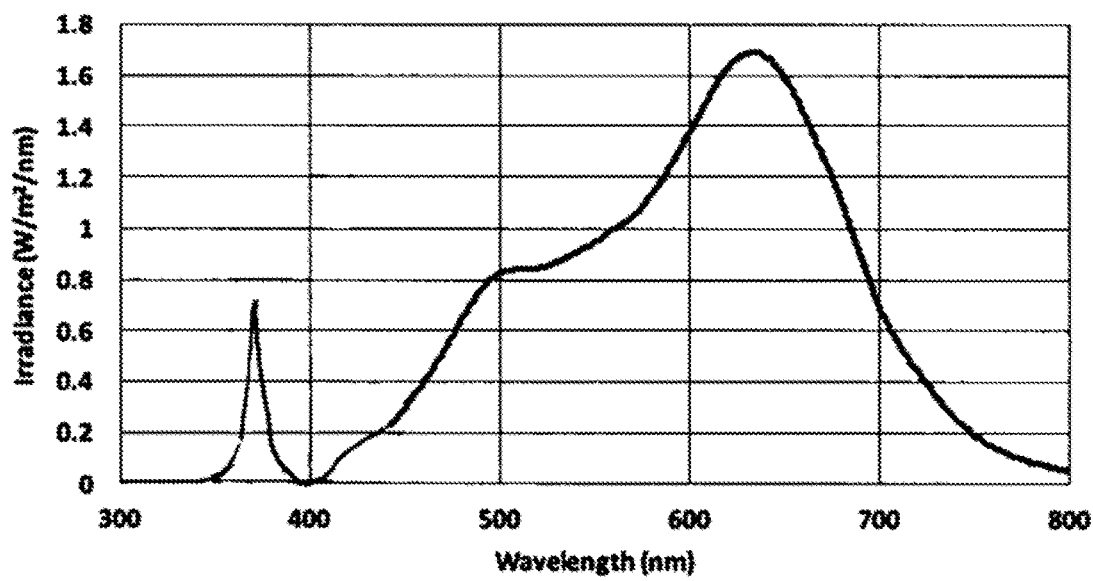
FIG. 13 is a spectrum of light emitted from a light-emitting element obtained by integrating the first light-emitting element and the second light-emitting element of the first embodiment.

Next, a configuration of the display device of this embodiment will be described using FIG. 9 to FIG. 13. It should be noted that FIG. 9 is an example of a spectrum of sunlight measured in an indoor environment irradiated with a fluorescent lamp, and FIG. 10 is an example of a spectrum of light measured in an outdoor environment during the day. FIG. 11 is an example of a spectrum of light emitted from a smartphone, and FIGS. 12A and 12B are each an example of a spectrum of light emitted from the display device of this embodiment. FIG. 13 is an example of a spectrum of light emitted from a light-emitting element obtained by integrating the first light-emitting element and the second light-emitting element of this embodiment.

<Display Device>

The display device 1 of this embodiment is not particularly limited as long as the device includes a display screen 2 that displays an image. Examples of the display device 1 include, for example, a smartphone, a game console, a personal computer, a liquid crystal television, and other display devices (for example, a display, a monitor, and the like used in various applications).

With the widespread use of portable terminal devices, such as game consoles and smartphones, and personal computers in recent years, light emitted from these devices (that is, the display device 1) of this embodiment is irradiated onto the eyes for a long period of time. In particular, the display device 1 of this embodiment is capable of controlling an emission wavelength in accordance with living situation and usage conditions, and thus irradiating light having the above-described specific wavelength, which is missing in a modern lifestyle, toward the eyes of the user.

<First Light-Emitting Element>

The first light-emitting element 6 is a light-emitting element that emits light used for image display. This first light-emitting element is known as a light-emitting element for displaying an image on the display screen 2 of a smartphone or the like, and is not particularly limited as long as one of these known light-emitting elements. Basically, the first light-emitting element 6 includes components such as color filters of each of three primary colors of red (R), green (G), and blue (B), liquid crystals, an alignment film, and electrodes, and has a structure that emits light of the three primary colors as a whole.

It should be noted that the display device 1 of this embodiment is configured, in such a first light-emitting element 6, to be capable of arbitrarily controlling the emission of each color to display various colors, and displaying an image or a moving image.

Further, the display device 1 is also configured to be capable of producing pseudo white light close to sunlight by predetermined pixel control. However, the light emitted by the first light-emitting element 6 includes almost no VL 7 within the range of 360 nm to 400 nm, inclusive.

<Second Light-Emitting Element>

The second light-emitting element 3 is a light-emitting element that irradiates the light (VL) 7 within the wavelength range of 360 nm to 400 nm, inclusive, toward the user 50. According to the spectral irradiance of sunlight illustrated in FIG. 10, this VL is included, for example, at about 6.8 W/m$^2$ in the horizontal direction facing south in 12:00 measurement data during clear weather in Tokyo, and enters the eye when the person is outdoors during the day.

On the other hand, as illustrated in FIG. 9, a lighting fixture that emits VL indoors is basically non-existent except when an incandescent bulb, a halogen lamp, or the like is installed. Further, in recent years in particular, longer amounts of time are spent indoors, and VL is overwhelmingly lacking. The display device 1 of the present application is configured to be capable of irradiating the lacking VL toward the user 50. Therefore, the display device 1 of this embodiment can suppress the onset and the progression of myopia. It should be noted that while, in Non-Patent Document 6, outdoor activity of 14 hours or more per week is described to significantly decrease the probability of the onset of myopia, the wavelength component effective in this regard is not specified.

In view of this point, assuming an irradiance of 3.1 W/m$^2$ based on an integrated value of VL within the range of 360 nm to 400 nm, inclusive, in terms of the value on the surface of the eyeball, when a person is exposed to VL for two hours per day, the dose of light to which the eye is exposed per day is calculated to be 23,320 J/m$^2$. While a VL irradiance less than 0.5 W/m$^2$ is also acceptable as long as the hours of outdoor VL exposure are long, the irradiance defined here is for a case of about two hours of exposure per day.

When the irradiance of the light is calculated by measuring the spectral irradiance of sunlight and using the irradiance of the sunlight as a reference, the VL intensity (irradiance) of sunlight of 360 nm to 400 nm, inclusive, for example, is 28.0 W/m$^2$ according to calculations on the basis of international standard data (AM 1.5). However, this value indicates a measured value when measured with a detection probe of an illuminometer facing the sun. As an actual measured value, for example, the VL intensity (irradiance) of sunlight of 360 nm to 400 nm, inclusive, at noon (12:00 PM) on Jun. 7, 2015 was 1.4 W/m$^2$ in the horizontal direction facing north. In particular, the dose (energy amount; J/m$^2$) is expressed as Irradiance (W/m$^2$)×Time (seconds).

(VL Irradiance)

The VL irradiance differs according to the usage environment of the smartphone or the like. When, for example, the smartphone or the like is used outdoors during the day, a sufficient VL of about 1.4 (horizontal facing north) to 6.8 (horizontal facing south) W/m$^2$ from sunlight exists in the environment, whether the weather is sunny or cloudy, and thus VL irradiance from the smartphone or the like is considered not required. In particular, this measured value is a temporal value of a sunny day and thus, when the sunlight is blocked by clouds, the measured VL value decreases to close to "0." For this reason, in such a case, preferably VL is irradiated from the smartphone as necessary.

In this case, for example, preferably the VL irradiance around the user or in the vicinity of the eyes of the user is measured by a sensor described later, the user is informed that the surrounding VL value by an image, a character string, or sound is low as necessary, and the second light-emitting element 3 emits light when a predetermined input operation is performed by the user, causing VL to be irradiated onto the eyes of the user.

When a smartphone or the like is used indoors, such as in an office or a house, during the day, preferably VL is irradiated from the smartphone or the like since a sufficient amount of VL does not exist indoors. At this time, the irradiance of the irradiating VL is preferably controlled in accordance with the illuminance of the VL in the usage environment. For example, because there is basically no emission of VL from a lighting device indoors, preferably the smartphone or the like is capable of irradiating, for example, a VL of about 3.1 W/m$^2$, which is close to sunlight.

The second light-emitting element 3 emits light including light (VL) within the range of 360 nm to 400 nm, inclusive, but need only mainly emit light having a wavelength within that range. It should be noted that "mainly" means, for example, that the irradiance need only be about 3.1 W/m$^2$, which is close to sunlight, within the wavelength range of 360 nm to 400 nm, inclusive, for example, and the entire range may or may not have an irradiance in the above-described range.

Further, the second light-emitting element 3 may emit light at wavelengths across the entire range of 360 nm to 400 nm, light within the range of 360 nm to 400 nm and including a bottom portion of the spectrum as illustrated in FIG. 12A, for example, such as light within the range of 350 nm to 410 nm, for example, or, of the light within the range of 360 nm to 400 nm, only light within the range of 370 nm to 390 nm, for example.

That is, the second light-emitting element 3 need only "mainly" emit light within a wavelength range of 360 nm to 400 nm, inclusive. Examples of specific elements include a shell type LED (for example, an LED manufactured by Nichia Corporation, peak wavelength: 375 nm, example: NSPU510CS manufactured by Nichia Corporation), and a laser diode that emits a specific wavelength. However, the element is not limited to these. It should be noted that the spectrum data can be measured using various devices and methods. However, in the present application, the spectrum data was measured using the fiber multi-channel spectrometer "Blue Wave" manufactured by StellarNet, Inc.

<Third Light-Emitting Element>

The third light-emitting element is provided to the display device 1 as necessary, and is a light-emitting element that emits blue light (hereinafter abbreviated as "BL") within a range of 460 nm±20 nm. BL is blue light that acts so as to not disrupt the circadian rhythm. Generally, the term blue light refers to a range of 380 nm to 500 nm, according to the definition from the Blue Light Society, and the like.

According to the spectral irradiance of sunlight within that wavelength range, blue light within the range of 380 nm to 500 nm was, for example, in the measurement of sunlight at noon (12:00 PM) on Jun. 7, 2015, included at about 8.7 W/m$^2$ at the horizontal facing north at 12:00 during clear weather in Tokyo, as illustrated in FIG. 10. Therefore, BL within the range of 460 nm±20 nm can enter the eyes from sunlight when a person is outdoors during the day, and regulate the circadian rhythm.

On the other hand, even when a person works indoors or the like, as illustrated in FIG. 9, BL is emitted from a lighting device such as a fluorescent lamp and, according to the spectral irradiance of a white fluorescent lamp installed on the ceiling in an office, for example, is included at about 0.1 W/m$^2$ (the value of 380 nm to 500 nm, which is the wavelength region of blue light defined by the Blue Light Society and the like, similar to the above). Nevertheless, there is a significant difference between the BL entering the eyes from sunlight and the BL entering the eyes from a fluorescent lamp, and the display device 1 according to the present invention can irradiate BL for offsetting that difference toward the eyes.

BL need not be a blue light of 380 nm to 500 nm as defined by the Blue Light Society and the like and, in the present application, need only be emitted at least within the range of 460 nm±20 nm for regulating the circadian rhythm. As a result, with the BL within the range of 460 nm±20 nm, it is possible to regulate the circadian rhythm and stabilize appetite, drowsiness, sleep, and the like, eliminate stress as well, and maintain physical health.

Sunlight includes light having a wavelength in a wide range, as illustrated in FIG. 10. Therefore, irradiating light similar to sunlight onto the eyeball, regardless of day or night and without attention paid to the irradiance or the irradiation time, for the purpose of suppressing the onset and the progression of myopia results in exposure to light included in sunlight and having a wavelength that disrupts the circadian rhythm as well as light that damages the retina. For this reason, irradiating light similar to sunlight onto the eyeball, regardless of day or night and without attention paid to the irradiance or the irradiation time, is preferably avoided to the extent possible.

Further, compared to outdoors, VL within the range of 360 nm to 400 nm, inclusive, basically is non-existent indoors, as illustrated in FIG. 9.

The third light-emitting element irradiates BL within the range of 460 nm±20 nm, which acts so as to not disrupt the circadian rhythm. When a smartphone or the like is used mainly indoors for a long period of time, the circadian rhythm can be regulated without disruption by irradiating light within the range of 460 nm±20 nm, which is lacking during the day, toward the eyeball.

Even when measurement is made by actually bringing a measurement probe into contact with a liquid crystal display, at the value of 380 nm to 500 nm, which is the wavelength region of blue light defined by the Blue Light Society and the like, blue light of only about 1 W/m$^2$ is emitted from the smartphone, as illustrated in FIG. 11. However, this value is the measured value when the distance from the display screen is substantially "0."

While, in daily life, the light environment may be good or bad, when light within the range of 460 nm or greater, ±20 nm, is controlled so as to allow irradiation onto the eyes in accordance with the light environment during the day, the circadian rhythm is regulated, making it possible to impart a favorable effect on the eyes and body.

It should be noted that, while BL within the range of 460 nm±20 nm is mainly irradiated even with the third light-emitting element, "mainly" means that the irradiance, for example, need only be about, at most, 8.7 W/m$^2$, which is close to sunlight, within the wavelength range of 460 nm±20 nm, for example, and the entire range may or may not have an irradiance in the above-described range.

Further, the third light-emitting element may emit light at wavelengths across the entire range of 460 nm±20 nm, light within the range of 460 nm±20 nm and including a bottom portion of the spectrum as illustrated in FIG. 12B, for example, such as light within the range of about 420 nm to 540 nm, for example, or, of the light within the range of 440 nm to 480 nm, only light within the narrow range of 465 nm to 475 nm, for example.

That is, the third light-emitting element need only "mainly" emit light within a wavelength range of 440 nm to 480 nm, inclusive. Examples of specific elements include an LED (for example, an LED manufactured by Nichia Corporation, peak wavelength: 468 nm, example: NSCB455AT manufactured by Nichia Corporation), and a laser diode that emits a specific wavelength. However, the element is not limited to these.

The "irradiance of about 1 W/m$^2$ within the wavelength range of 460 nm±20 nm or less" described above is based on the fact that the value facing north within the range of 380 nm to 500 nm in sunlight is approximately 8.7 W/m$^2$ and approximately 1 W/m$^2$ within the wavelength range of 460 nm to 480 nm, inclusive.

(BL Irradiance)

BL irradiance differs according to the usage environment of the smartphone or the like. When, for example, the smartphone or the like is used outdoors during the day, a sufficient BL of about 8.7 (horizontal facing north) to 43.2 (horizontal facing south) W/m$^2$ exists in the usage environment, whether the weather is sunny or cloudy, as illustrated in FIG. 10. For that reason, BL irradiation from the smartphone or the like can be deemed not required.

On the other hand, when a smartphone or the like is used indoors, such as in an office or a house, during the day, a sufficient amount of BL does not exist indoors. For that reason, preferably BL is irradiated from the smartphone or the like. At this time, the irradiance of the irradiating BL is preferably controlled in accordance with the illuminance of the BL in the usage environment. For example, the irradiance of BL from a lighting device (fluorescent lamp) in an office is low, and BL of only about 0.1 W/m$^2$ is irradiated, for example.

In particular, as the measured value when separated from the display screen 2 of a normal smartphone by a distance L of 0 to 30 cm (as a value of 380 to 500 nm, which is the wavelength region of blue light defined by the Blue Light Society and the like), BL of only about 0.05 to 1 W/m$^2$ is irradiated. Therefore, from a smartphone, preferably BL up to about 10 W/m$^2$ can be irradiated in accordance with sunlight, allowing use in any usage environment.

The third light-emitting element need only emit light including BL within the range of 460 nm±20 nm, and preferably may be any element that mainly emits light within that wavelength region. Here, "mainly" means, in the case of BL within the range of 460 nm±20 nm, for example, the irradiance need only be about 1 W/m$^2$ in accordance with the sunlight within the range of 460 nm±20 nm. The entire range may or may not have an irradiance in the above-described range.

Examples of specific elements include an LED having a peak within the wavelength region and a laser diode that emits a specific wavelength within the wavelength region. However, the element is not limited to these.

<Installation Form of Light-Emitting Element>

The first light-emitting element is usually provided in a pixel of a display, normally includes RGB color filters, liquid crystals, an alignment film, an electrode, and the like as components, and has an element structure that emits light of the three primary colors as a whole.

On the other hand, the second light-emitting element or the second light-emitting element and the third light-emitting element can be installed in various forms, as illustrated in FIG. 1 to FIG. 4. It should be noted that, in the present application, the "second light-emitting element and the like" refers to the second light-emitting element and may include the third light-emitting element, and the "second light-emitting element" refers to only the second light-emitting element.

FIG. 1 is an example in which the second light-emitting element that emits VL is added to the first light-emitting element that emits the three RGB primary colors in the display screen of a smartphone or the like. In this case, the VL light-emitting element is preferably provided so as to allow emission of a necessary sufficient amount of light. Further, while BL can be emitted to a certain extent by a blue (B) light-emitting element, when the irradiance is low as in the case of a normal smartphone, an accessory or the like of the third light-emitting element is preferably separately provided in the same way as the second light-emitting element consisting of the accessory illustrated in FIG. 3. Preferably, the amount of BL from the liquid crystal display of the smartphone is compensated by providing such a third light-emitting element.

FIG. 2 is an example in which the second light-emitting element and the like are provided to a main body frame of a smartphone or the like, and FIG. 3 is an example in which the second light-emitting element and the like are attached as accessories to the main body frame of the smartphone or the like.

FIG. 4 is an example in which the second light-emitting element and the like are attached as accessories to a frame of a display main body of a personal computer. It should be noted that the installation form is not limited thereto, and is not limited as long as the same function is exhibited.

The second light-emitting element and the like may be a single light-emitting element integrated with the first light-emitting element or may be two or more light-emitting elements provided separately from the first light-emitting element.

In the installation form illustrated in FIG. 1, the pixels are separate, but the VL light-emitting element, which is the second light-emitting element, is integrated with the first light-emitting element that emits the three RGB primary colors.

In the installation form illustrated in FIG. 2, the LED or laser diode that emits VL is provided to the main body frame of a smartphone or the like as a separate part.

In the installation forms illustrated in FIG. 3 and FIG. 4, the LED or laser diode that emits VL is attached to the frame or the like of the smartphone or the like as accessories. It should be noted that form examples of the accessory include a form such as a laser pointer.

FIG. 5 and FIG. 6 are each an example of a mode in which the first light-emitting element and the second light-emitting element and the like are integrated. The light-emitting element illustrated in FIG. 5 causes fluorescent substances that emit RGB by excitation light having a wavelength within the range of 360 nm to 400 nm, inclusive, to illuminate, and emits white light as a whole.

This light-emitting element is an example of an element that is configured by an excitation light-emitting part (LED) that emits excitation light having a wavelength within the range of 360 nm to 400 nm, inclusive, and fluorescent substances of R (red), G (green), and B (blue) provided so as to cover the excitation light-emitting part.

A portion of the light (excitation light) having a wavelength within the range of 360 nm to 400 nm, inclusive, is transmitted through the fluorescent substances as illustrated. Such a light-emitting element appears white as a whole. That is, the light-emitting element can be treated as element obtained by integrating the first light-emitting element and the second light-emitting element and the like from wavelength components.

FIG. 13 is an example of a spectrum of light emitted from the integrated light-emitting element illustrated in FIG. 5. The drawing shows that excitation light having a wavelength within a range of 360 nm to 400 nm, inclusive, is emitted. Further, the light of 400 nm or greater is a spectrum of light emitted from the excited RGB fluorescent substances.

The light-emitting element illustrated in FIG. 6 includes the second light-emitting element that emits light having a wavelength within the range of 360 nm to 400 nm, inclusive, and the first light-emitting element that emits light of the three RGB primary colors. This light-emitting element is an example of an element that is configured by a light-emitting part that emits light having a wavelength within the range of 360 nm to 400 nm, inclusive, and the light-emitting parts (LEDs) of R (red), G (green), and B (blue). Such a light-emitting element can also be used as a light-emitting element obtained by integrating the first light-emitting element and the second light-emitting element and the like.

(Irradiation Mode)

Preferably, VL is irradiated toward the eyeball, and preferably BL is also irradiated toward the eyeball. It should be noted that, in the present application, "VL and the like" refers to VL and may include BL, and "VL" refers to VL only. To orient toward the eyeball, the second light-emitting element and the like are preferably provided toward the eyeball.

When an image or a moving image displayed on a display device such as a smartphone is viewed, there are many cases where the eye 51 is in a direction roughly normal from the center of the display screen 2, and thus the second light-emitting element and the like provided in the installation form described above are preferably provided so that VL and the like are irradiated in that direction.

Figure 7:
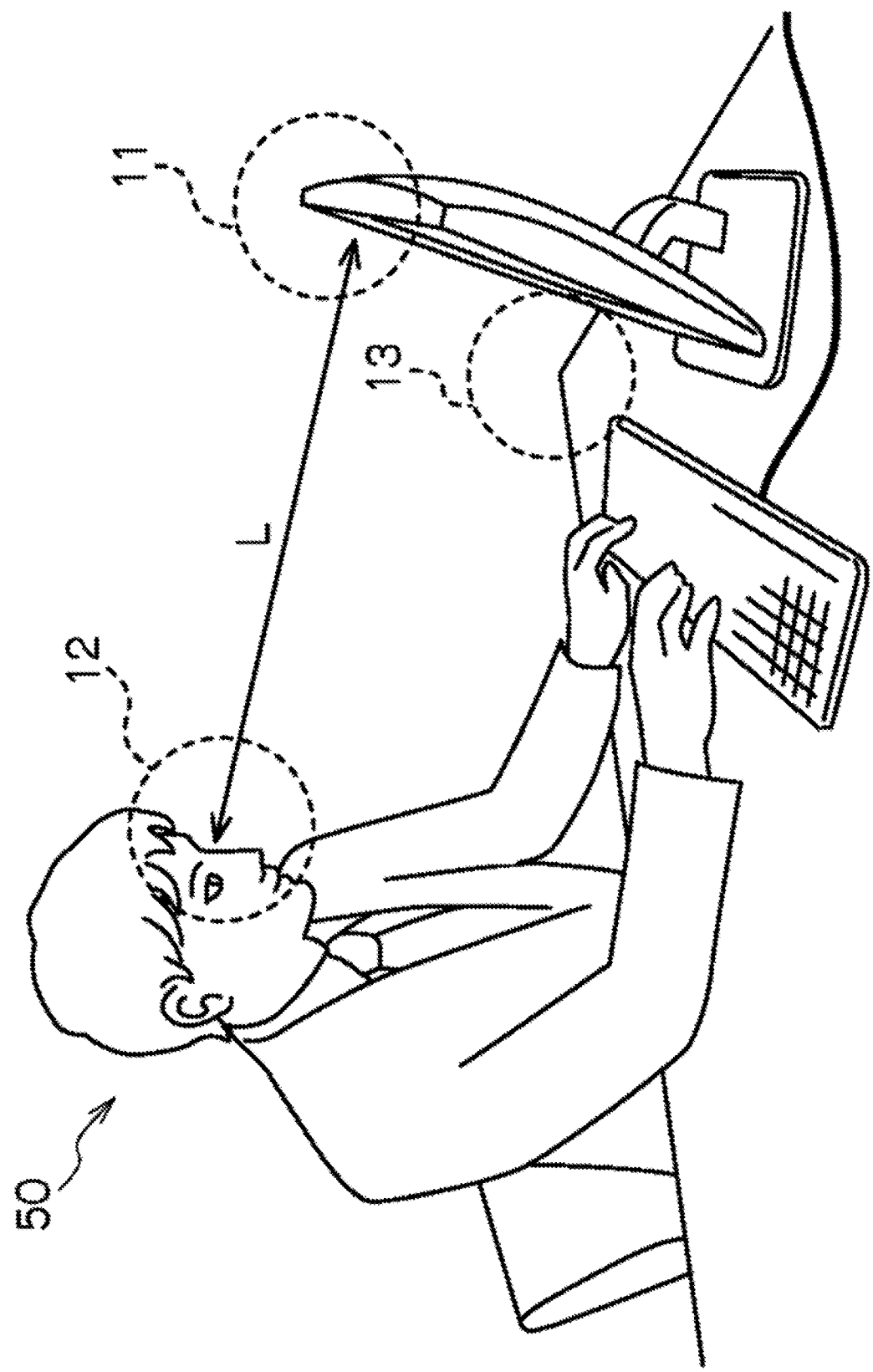
FIG. 7 is a schematic view illustrating an example of a form of measuring a usage environment in the first embodiment.

As illustrated in FIG. 7, preferably, the distance L from the display screen 2 of a smartphone or the like to the eye 51 is (1) about 100 mm to 500 mm in the case of a smartphone, for example, (2) about 300 mm to 700 mm in the case of a personal computer, for example, and (3) about 800 mm to 5,000 mm in the case of a television, for example, in accordance with the size of the television, and the irradiation direction and the irradiance of VL and the like are designed in consideration of the distance L. It should be noted that it is also possible to automatically measure the distance L from the display screen 2 to the eye 51, and automatically adjust the irradiation direction of the VL and the like from the light-emitting element.

Specifically, it is also possible to automatically measure the distance L to the eye and the position by a camera or image sensor mounting or mounted on a smartphone or a personal computer, for example, and automatically adjust the irradiation orientation of the light-emitting element and the intensity of the light on the basis of the measurement result.

To measure the distance L from the display screen 2 to the eye 51, for example, a measuring device such as a complementary metal oxide semiconductor (CMOS) sensor, a charge-coupled device (CCD) sensor, or an infrared sensor can be applied.

Because the irradiance of the VL and the like entering the eye and the dose (also referred to as the light energy amount) differ according to the distance L to the eye, an irradiance set to a preferred value can be irradiated onto the eyes by measuring that distance L. In particular, the light-emitting element may be a configuration in which, when the distance L is a predetermined threshold value (20 cm, for example) or less, a warning such as "The screen is too close. Use the device at a greater distance." is issued by an image, a character string, sound, or the like.

Further, it is also possible to automatically determine or automatically measure whether or not the eyes are facing the screen, the number of blinks, and the time required for blinking, and thus, accurately accumulate the irradiance of VL and the like reaching the eyes.

Irradiation can be ended when a set dose is reached by measuring the time when the light is actually irradiated onto the eyes and setting a dose in advance.

Thus, preferably the irradiance is corrected in accordance with the distance L from the eye of the user and/or the direction of the eyes, and the like by including a measuring device (also referred to as a sensor) that measures the distance L and/or the direction. As a result, it is possible to irradiate the lacking light in the dose required with the actual form of use.

<Irradiation Control in Accordance with Usage Environment>

(Usage Environment)

Irradiation of the VL and the like is controlled and performed by the second light-emitting element and the like in accordance with the usage environment. The usage environment refers to the environment in which the smartphone or the like is used, and is, for example, outdoors or indoors, in an office, a school, or a home, sunny, cloudy, or rainy weather when outdoors, day or night, a living room, a library, or a study when indoors, and the like.

Preferably, the insufficiency or excess of VL and the like already existing in the environment is predicted or measured according to these usage environments, and VL and the like in an amount equivalent to the insufficiency is irradiated. When a device such as a smartphone is connected to the Internet, the information of the environment (weather) at that location can also be acquired from the Internet, stored in storage means, such as memory (not illustrated) as a log, and reflected in irradiation conditions.

Further, preferably the irradiance of sunlight or the light of lighting around the user is measured at the position of the eyes of the user by a sensor, making it possible to adjust the illuminance of the display light when an image is displayed on the display screen in accordance with the measurement result.

Various sensors 8 and the like can be used for measuring the usage environment. For example, the various sensors 8 and the like can specify position information by a global positioning system (GPS), and specify when the usage environment is clearly outdoors, clearly indoors, or the like. Further, the various sensors 8 and the like can measure irradiance by an optical sensor and, with information from the Internet and the like as well, specify whether the usage environment is outdoors or indoors, sunny, cloudy, or rainy, the extent of the illuminance, and the like.

It should be noted that such sensors 8 may be integrally provided to the main body frame of the smartphone or the like, or attached to the main body frame as separate part accessories.

Further, by providing such sensors, it is possible to identify the usage environment and irradiate VL and the like at a preferred illuminance and for a preferred time. Examples of the time include a continual irradiation time, an irradiation timing, an accumulated irradiation time, and the like.

By identifying the usage environment, it is possible to irradiate light lacking in the usage environment at a predetermined irradiance. For example, in a usage environment where BL is lacking within the range of 460 nm±20 nm during the day, disruption of the circadian rhythm can be suppressed by irradiating BL having that wavelength at a predetermined irradiance. In particular, during indoor desk work, because BL of that wavelength region decreases, it is possible to compensate for the insufficiency.

(Sensor)

The sensors 8 are preferably provided as necessary. Preferable examples of the sensors 8 include an illuminance sensor that detects visible light as illuminance (lux), a specific wavelength detecting optical sensor that detects irradiance of a specific wavelength (violet light or blue light, for example), and the like.

While the illuminance sensor or the specific wavelength detecting sensor may be used alone, preferably both sensors are included.

With the illuminance sensor alone, only light and shade can be distinguished, not whether the usage environment is an outdoor location (during the day) or a bright indoor location. Nevertheless, by combining an illuminance sensor with, for example, a violet light sensor, it is possible to easily distinguish whether the location is outdoors or indoors since light close to 380 nm is usually non-existent indoors.

The sensors 8 can accurately identify the usage environment, and therefore automatically control the emitted VL and the like and the illuminance thereof in accordance with the usage environment. It should be noted that the sensor 8 is configured to be controllable by the control unit 10 using an application program built into the smartphone or the like.

Further, the direction of the line of sight, the direction of the face, blinking, and the like are detected using a camera (an image sensor camera facing the direction of the user, for example) attached to the smartphone or the like. For example, if the face is facing downwards or deviates significantly from the optical path of the emitted light, the sensors 8 are configured to perform control in linkage with the control unit 10 so that light is not emitted in order to reduce consumption of the energy of the light.

Further, when it is necessary to deliver light to the back of the eye (to the retina), the sensors 8 can also be configured so that light is emitted only when the line of sight is toward the smartphone.

Furthermore, the sensors 8 can also be configured so that, when an area other than the face of the user is also imaged by the camera, the image of the user is matched with a predetermined pattern to detect the posture of the user, and the user is determined to be slouching or the like, a warning such as "Your posture is poor. Please correct your posture." is issued to the user by an image, a character string, sound, or the like.

(Irradiation Management)

The control unit 10 is preferably executed by an application program that acquires and manages the data of VL irradiated from the second light-emitting element. Further, the control unit 10 may have a function that further acquires and manages the data of BL irradiated from the third light-emitting element using the application program.

Thus, the control unit 10 is configured to be capable of acquiring data of the light environment and managing the history of irradiation onto the user by using the application program described above.

Further, when a device such as a smartphone is connected to the Internet, the control unit 10 can also acquire data of the light environment in that location from the Internet, store the history of irradiation onto the user in storage means, such as memory (not illustrated) as a log, and reflect the data in irradiation conditions.

As a result, it is possible to conduct evaluations by associating the irradiation history and, for example, life rhythm management and eye test results.

Furthermore, preferably the control unit 10 acquires and manages the measurement results of the usage environment by the application program. As a result, it is possible to conduct evaluations by associating the data of VL and the like in accordance with the usage environment.

As an application, the control unit 10 may be configured to be capable of detecting the temperature of the eyeball surface, the degree of wetness, the frequency of blinking, and the like by sensors provided to the display device, measuring the degree of dry eye by image analysis, and irradiating red to infrared light, which is effective for alleviating dry eye, onto the eyes.

Further, the control unit 10 may be configured to collect acquired data on a server via the Internet and statistically process and analyze the data of a large number of users. With such an analysis, it is possible to acquire a large amount of data and use the data for clinical research.

Figure 8:
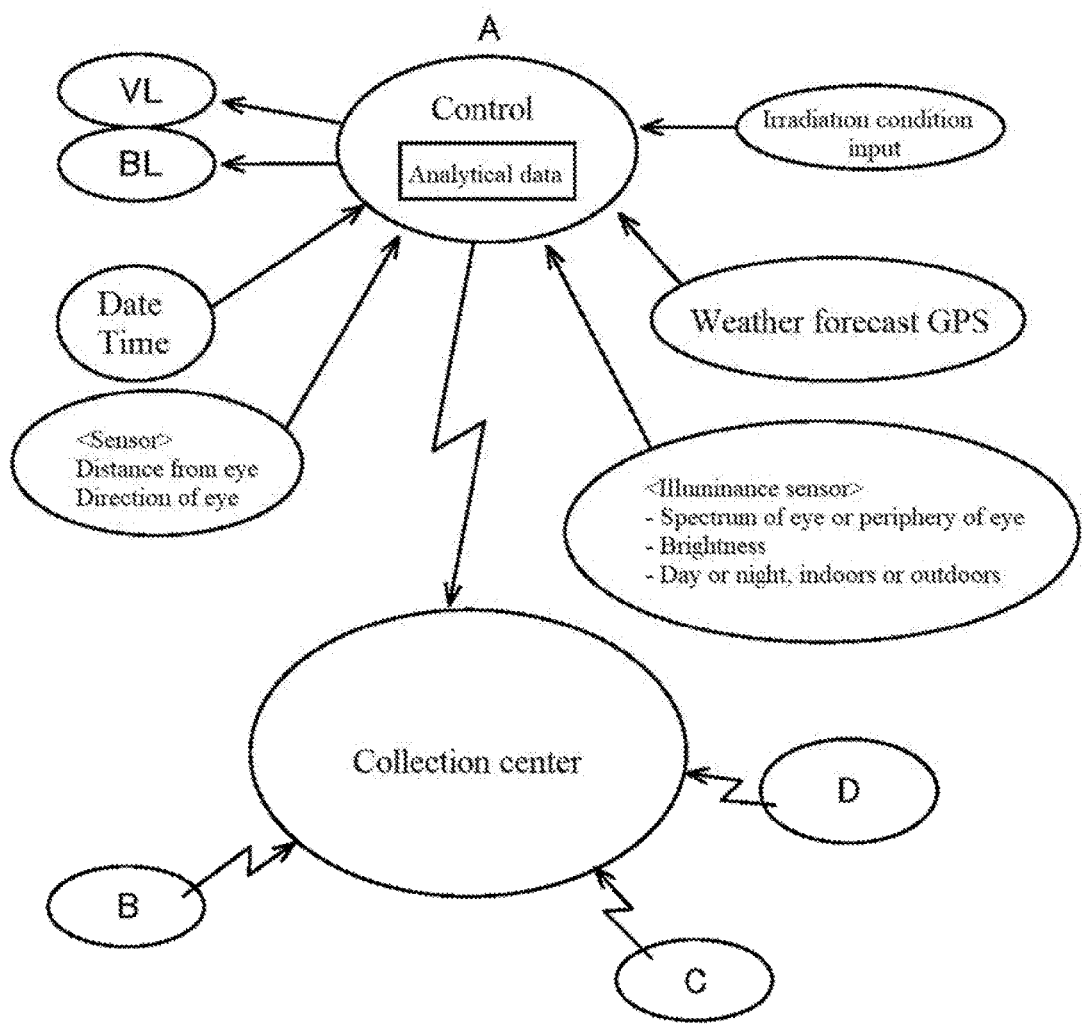
FIG. 8 is a schematic view of controlling the emission of light having a specific wavelength in the first embodiment.

Further, as illustrated in FIG. 8, the display device 1, by being provided with the various sensors 8 and further linked with GPS information, is configured to be capable of monitoring a situation on a time axis from the measurement data of the sensors 8, and storing the monitoring information.

By conducting a comparative analysis of such monitoring information with the database through the cloud, the display device 1 can show a display such as "Your eyes are currently in such-and-such a state. Try to increase your outdoor activity," and give feedback (advice) to the user.

Further, as long as this monitoring information is managed in a collection center (refer to the second embodiment) through the Internet, the display device 1 is configured to be capable of providing advice to the user by a doctor, a parent, a teacher, or other person responsible for protection as well using the display device 1, on the basis of the monitoring information.

Furthermore, when a plurality of display devices (smartphones or the like) A to D are capable of collection, it becomes also possible to acquire data related to the suppression of the onset and progression of myopia, which is very promising as a global myopia problem measure.

<Other Light>

The light-emitting element may have a wide wavelength region of light, and not allow selective irradiation of the VL and the like described above. In such a case, it is possible to selectively irradiate only a specific wavelength using a filter or the like, or selectively irradiate VL and the like as described above by suppressing irradiation.

Further, as necessary, light around 435 nm or light around 505 nm may be restricted. The display device further include the control unit 10 that restricts at least one or both of light within a range of 435 nm±10 nm and light within a range of 505 nm±10 nm, thereby making it also possible to restrict light around 430 nm or light around 505 nm to which the retina is highly sensitive.

Thus, while it may be desirable to control the light such as mentioned above emitted from the first light-emitting element depending on the usage environment in order to suppress an adverse effect that may occur due to eye exposure to light, it is also possible, according to the display device of the present application, to intentionally restrict and irradiate, of the light emitted from the first light-emitting element, light having an applicable specific wavelength toward the eyes of the user.

Further, in this embodiment, the display device may be configured to irradiate infrared light, near infrared light, and far infrared light as necessary.

[2] Second Embodiment

[2.1] General Configuration

Figure 14:
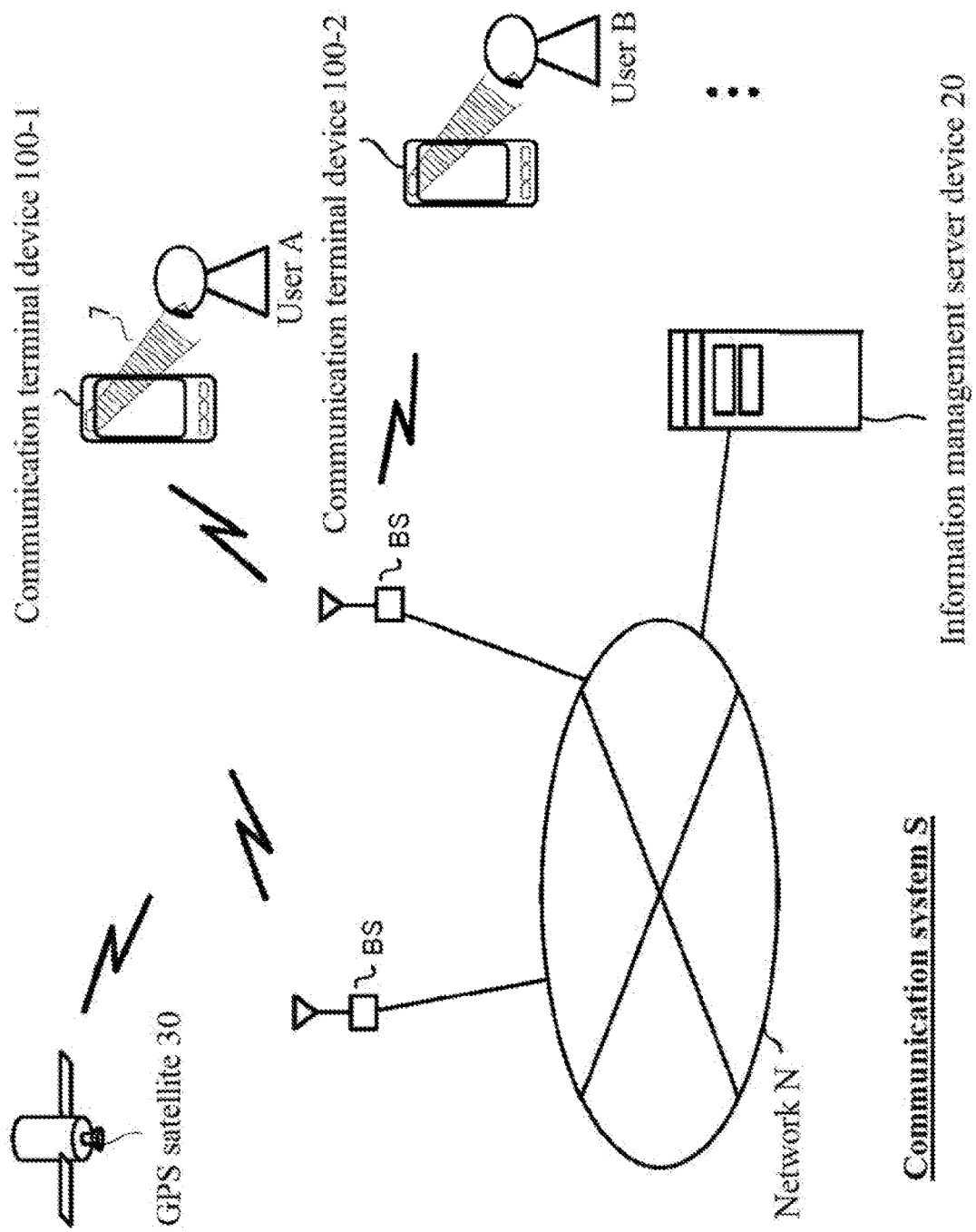
FIG. 14 is a system configuration diagram illustrating an example of a communication system of a second embodiment of the present application.

An overview of a communication system S of a second embodiment of the present invention will now be described using FIG. 14. It should be noted that FIG. 14 is a system configuration diagram illustrating a configuration of the communication system S of this embodiment, and only a predetermined user and a communication terminal device 100 are illustrated to prevent complexities in drawing. That is, in the communication system S, there exists a greater number of users and communication terminal devices 100 than illustrated. Further, in this embodiment, the same members as those in the first embodiment are denoted using the same reference numbers, and descriptions thereof are omitted.

The communication system S of this embodiment is a communication system that uses the display device 1 of the first embodiment as the communication terminal device 100 and, at the time of displaying and providing a predetermined image to the user, irradiates VL onto the eyes of the user, thereby effectively suppressing the occurrence and progression of myopia.

Further, the communication system S is configured by, for example, the communication terminal devices 100 having the various functions of a terminal device that can be carried by a user as well as the functions of the communication terminal device 100 of the first embodiment, and an information management server device 20 that achieves a providing function of providing information to each of the communication terminal devices 100 via a network N, as well as the function of the collection center of the first embodiment.

The communication terminal device 100 of this embodiment is a communication terminal device such as a smartphone or a tablet type information communication terminal device carried by a user.

Further, the communication terminal device 100 is configured to irradiate VL onto the eyes of the user by the second light-emitting element 3 of the display device 1 while displaying various images on the display screen 2 of the first light-emitting element 6 mounted on the display device 1.

Then, the communication terminal device 100, for example, as illustrated in FIG. 1 and FIG. 2, is provided with the second light-emitting element 3, configured as illustrated in FIG. 5, on a main body frame 4 surrounding the display screen 2 in the same manner as in the first embodiment.

Furthermore, the communication terminal device 100 is equipped with various application programs including a Web browser for displaying data described using a markup language such as extensible markup language (XML) in a format viewable by the user.

Then, the communication terminal device 100 is configured to perform data communication with the information management server device 20 and other server devices (such as a server device for distributing weather information, for example; not illustrated) connected to the network N, and execute display processing and the like for data received via the network N.

In particular, to carry out appropriate VL irradiation onto the eyes of the user, the communication terminal device 100 of this embodiment is configured to execute:

(1) Personal data management processing for storing a behavior history (life log) of the user over a predetermined period (one day, for example) and managing personal data indicating the stored life log;

(2) Dosed VL energy amount calculation processing for calculating the energy amount to which the user was exposed from the sun (hereinafter referred to as "dosed VL energy amount") within a predetermined past period on the basis of the stored personal data;

(3) Dose insufficiency calculation processing for comparing a dose of VL that a user is recommended to take (hereinafter referred to as "recommended dose") in a predetermined period (one day, for example) in order to suppress the onset and progression of myopia with the dosed VL energy amount specified in the dosed VL energy amount calculation processing, and calculating the insufficiency with respect to the recommended dose; and (4) VL irradiation control processing for controlling VL irradiation onto the user on the basis of the dose insufficiency calculated by the dose insufficiency calculation processing.

The information management server device 20 has a function of the collection center of the first embodiment, and has a function of collecting and managing data corresponding to the irradiation history of the VL irradiated onto the eyes of the user from each communication terminal device 100 to present the data to operators such as doctors, parents, teachers, advocates, and other persons responsible for protection using various terminal devices (not illustrated).

Further, the information management server device 20 is configured to allow use for collecting and providing monitoring information, and monitoring actual visual acuity measurement results and the VL irradiation history to examine the relationship between the amount of VL irradiation and the occurrence and progression of myopia, and the like.

It should be noted that, in this case, for example, as long as an objective index value indicating a degree of myopia, such as an axial length, is input by the operator, and the index value and the monitoring result of VL are managed and collected in association with other input/output (I/O), the objectivity of the monitoring results can be ensured.

[2.2] Communication Terminal Device

Next, a configuration of the communication terminal device 100 of this embodiment will be described using FIG. 15. It should be noted that FIG. 15 is a block diagram illustrating a configuration example of the communication terminal device 100 of this embodiment.

Figure 15:
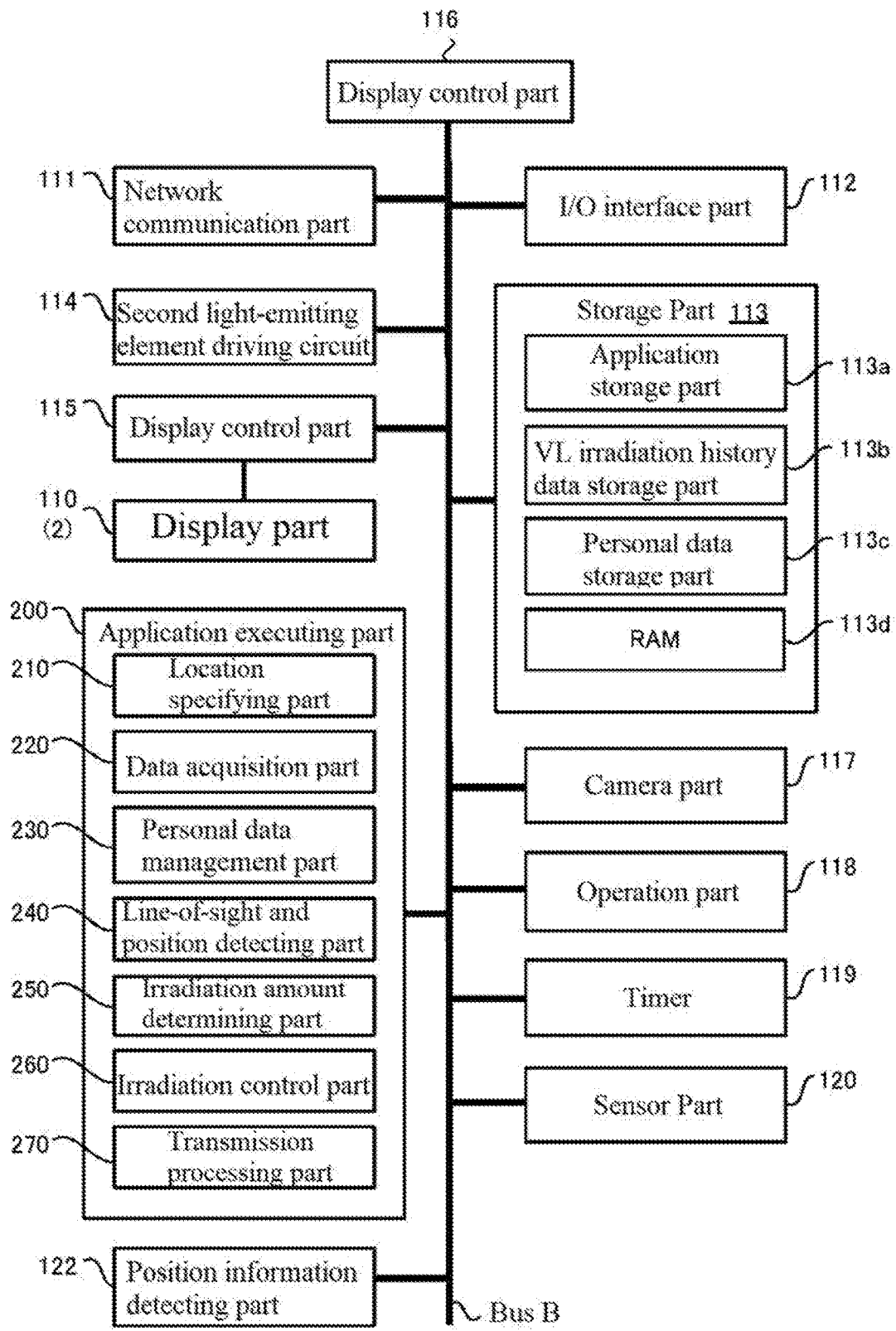
FIG. 15 is a block diagram illustrating a configuration example of a display device of the second embodiment.

As illustrated in FIG. 15, the communication terminal device 100 of this embodiment includes a display part 110 constituting the display screen 2, a network communication part 111 communicably connected to the network N, an I/O interface part 112, a storage part 113 for storing data corresponding to various information, and a second light-emitting element driving circuit 114 for driving the second light-emitting element 3 having the configuration of FIG. 5.

Further, the communication terminal device 100 includes a display control part 115 for controlling the display of an image on the display screen 2, a management control part 116, a camera part 117 for capturing an image, an operation part 118 configured by a touch panel, and a timer 119 for specifying the current date and time.

Furthermore, the communication terminal device 100 includes a sensor part 120 provided with various sensors including a VL illuminance sensor, a position information detecting part 122 that generates position information of the current location of the user, and an application executing part 200 that executes processing such as the above-described personal data management and VL irradiation control.

It should be noted that the parts described above are connected to one another by a bus B, and send and receive various data and signals.

The display part 110 is configured by a liquid crystal panel or an organic electroluminescence (EL) display panel.

The network communication part 111 is a predetermined network interface, and sends and receives various data with the information management server device 20 and various server devices (not illustrated) connected to the network N via a base station BS under the control of a terminal management control part 180 and the application executing part 200.

The I/O interface part 112 is, for example, an input/output interface of a universal serial bus (USB), a wireless local area network (LAN; IEEE 208.11a, b, n, ac), or the like.

In particular, the I/O interface part 112 relays the transfer of data between a connected external device (not illustrated) and the bus B.

Then, the I/O interface part 112 is used to transmit various commands to a wearable terminal device (not illustrated) on the basis of instructions from the user, and acquire data related to the heartbeat and the like of the user from the wearable terminal device.

The storage part 113 is, for example, configured by electrically erasable programmable read only memory (EEPROM), flash memory, or the like.

Then, the storage part 113 includes an application storage part 113a for storing various application programs including a personal data management application program and a VL irradiation control application program, a VL irradiation history data storage part 113b for storing VL irradiation history data, a personal data storage part 113c for storing personal data, and a random-access memory (RAM) 113d used as a work area.

In particular, the VL irradiation history data storage part 113b, for example, stores VL irradiation history data obtained by associating a date with the illuminance and the period (that is, energy amount) when the second light-emitting element 3 emits light on the date.

The display control part 115 executes various controls for displaying an image on the display part 110 constituting the display screen 2.

In particular, in a case where the display control part 115 irradiates BL onto the eyes of the user in order to regulate the circadian rhythm, and displays an image on the display screen 2 in a time band during the day, the display control part 115 may, by display processing, increase the irradiation amount of the BL component and irradiate BL in an irradiation amount appropriate for the eyes of the user.

The management control part 116 is mainly configured by a central processing unit (CPU), and integrally controls each part of the communication terminal device 100.

The camera part 117 includes a lens, a flash, a shutter, and an optical system (not illustrated) for adjusting the lens focus, a zoom, and target focal point, and has a so-called camera function for a digital camera.

The operation part 118 is configured by various confirmation buttons, operation buttons for inputting various operation commands, a large number of keys such as a numeric keypad, and a touch panel, and is used when performing each operation.

The timer 119 specifies the current date and time, and is used to time the outdoor location period.

The sensor part 120 is configured by the sensors 8 of the first embodiment, including the VL illuminance sensor.

The position information detecting part 122 is configured by a GPS receiver, and generates position information of the user on the basis of the GPS signal received from a GPS satellite 30.

It should be noted that, in this embodiment, the method for specifying whether the user is indoors or outdoors on the basis of position information is not limited to these. For example, the position information detecting part 122 may execute an application program for map display, plot the current location corresponding to the position information on the map in the communication terminal device 100, and specify whether the user is indoors or outdoors.

Further, the position information detecting part 122 may transmit the position information to a server device for map display that exists on the network N, specify whether the current location is indoors or outdoors by the server device, and acquire the specified result from the server device.

The application executing part 200 is configured by a CPU that is the same as or independent from the management control part 116.

Then, the application executing part 200 implements each function by executing various application programs stored in the application storage part 113a under the control of the management control part 116.

Specifically, the application executing part 200, by executing the personal data management application program and the VL irradiation control application program, realizes:

(1) a location specifying part 210 for specifying the location of the user;
(2) a data acquisition part 220 for acquiring various data;
(3) a personal data management part 230 for managing personal data;
(4) a line-of-sight and position detecting part 240 for detecting the line-of-sight direction and position of the eyes;
(5) an irradiation amount determining part 250 for executing the dosed VL energy amount calculation processing and dose insufficiency calculation processing;
(6) an irradiation control part 260 for executing the VL irradiation control processing; and
(7) a transmission processing part 270 for transmitting various data.

It should be noted that details of the application executing part 200 of this embodiment will be described later.

[2.3] Application Executing Part

Next, the details of the application executing part 200 of this embodiment will be described.

(Location Specifying Part)

The location specifying part 210 specifies the current location of the user from position information detected by the position information detecting part 122, and specifies whether the current location is indoors or outdoors.

Further, when specifying whether or not the current location is outdoors, the location specifying part 210 controls the sensor part 120 to measure the irradiance of the VL around the user and, when the location is outdoors and the VL irradiance exceeds a threshold value α, specifies the location of the user as outdoors.

In particular, because the accuracy of position information changes depending on a reception state of the GPS signal, it is difficult to specify with high precision whether the user is indoors or outdoors on the basis of the GPS signal alone.

Further, as mentioned above, the light beam irradiated from a lighting fixture includes no or only a very small amount of VL, and thus the measured values of VL measured by the sensor differ greatly when the user is indoors and when the user is outdoors.

Here, the location specifying part 210 of this embodiment specifies that the user is outdoors when the current location of the user is outdoors and a predetermined threshold value α ($0.2$ W/m$^2$ or the like, for example) is exceeded.

(Data Acquisition Part)

The data acquisition part 220 is linked with the network communication part 111, and acquires weather information and VL measured value data corresponding to the current location of the user from an external source on the basis of the position information detected by the position information detecting part 122.

It should be noted that the method for acquiring weather information and VL measured value data is arbitrary and, for example, the data acquisition part 220 transmits position information to a server device (not illustrated) for weather information management provided on the network N, and acquires the weather information corresponding to the current location transmitted on the basis of the transmitted position information.

Further, the data acquisition part 220 transmits the weather type (sunny, cloudy, rainy, or the like) indicated by the weather information and the position information to the information management server device 20 and acquires, among the VL measured value data corresponding to the location of the user, VL measured value data corresponding to the weather type on the basis of the transmitted weather type and position information.

(Personal Data Management Part)

The personal data management part 230 stores the position information of the user obtained by the position information detecting part 122 in association with a time as personal data (a life log) per predetermined period (per minute, for example) in the personal data storage part 113c.

Further, the personal data management part 230 stores the result of the indoor/outdoor determination of the current location of the user detected in the location specifying part 210 in association with the position information as personal data in the personal data storage part 113c.

It should be noted that the personal data management part 230 may store, instead of the indoor/output determination result, or along with the indoor/outdoor determination result, according to various sensors of the sensor part 120 or an operation of the user, the VL irradiance received by the sensor part 120 at that time in the personal data storage part 113c as an irradiated VL dose.

(Line-of-Sight and Position Detecting Part)

The line-of-sight and position detecting part 240 specifies the position of the eyes, the direction of the line of sight, the open/closed state of the eyelids, and the distance to the eyes of the user while linked with the camera part 117.

It should be noted that the method for detecting the position of the eye, the line of sight, the open/closed state of the eyelids, and the distance to the eye is the same as in the related art, and therefore the details are omitted.

Then, when the display device is configured so that the line-of-sight and position detecting part 240 detects the open/closed state of the eyelids of the user and the second light-emitting element driving circuit 114 irradiates VL only when the eyelids of the user are open, it is possible to reliably irradiate the VL onto the eyes of the user and prevent wasteful VL irradiation, and thus achieve power saving.

Further, the line-of-sight and position detecting part 240 of this embodiment, for example, constitutes the "detecting means" of the present invention.

(Irradiation Amount Determining Part)

The irradiation amount determining part 250 executes the dosed VL energy amount calculation processing and dose insufficiency calculation processing.

Specifically, the irradiation amount determining part 250 acquires personal data generated by personal data generation processing, and calculates the irradiated VL dose information indicating the energy amount of VL irradiated onto the user during a predetermined period on the basis of the acquired personal data.

That is, the irradiation amount determining part 250 calculates the dose (estimated amount) of VL received by the user from the sun within the past 24 hours while taking into consideration the weather, on the basis of the location of the user and whether that location is indoors or outdoors, for each predetermined period (one minute, for example).

Basically, the outdoor irradiance of VL changes according to the current location of the user. For example, the outdoor irradiance of VL in Hokkaido (an area located in the northern area of Japan) and the outdoor irradiance of VL in Okinawa (an area located in the southern area of Japan) are different.

Further, when the weather is different even in the same area, the outdoor irradiance of VL changes.

For example, when the outdoor irradiance of VL in Tokyo (an area located approximately at the center of Japan) was measured several times per hour from 11:00 to 14:00 with respect to each horizontal direction of north, south, east, and west, the average of the measured values was calculated for the four directions, and the average value in the time bands of 11:00 to 14:00 was calculated, the following values were obtained:

(A) Average value on clear day: 5.83 $W/m^2$
(B) Average value on cloudy day: 2.71 $W/m^2$ That is, in Tokyo, it is understood that the irradiance is more than twice as high in a clear environment as compared to a cloudy environment. It should be noted that, since the value during clear weather is an average value of the period from 11:00 to 14:00, the value differs from the irradiance (6.83 $W/m^2$) at noon in Tokyo mentioned above.

Thus, since the outdoor irradiance of VL changes in accordance with the current location of the user and the weather, the irradiance of VL in each area, in this embodiment, is measured in advance for each weather type, and data indicating the measurement result (hereinafter referred to as "VL measured value data") is configured to be registered in the information management server device 20.

Then, the irradiation amount determining part 250 specifies the weather at the current location of the user and acquires, of the VL measured value data corresponding to the current location, the VL measured value data corresponding to the specified weather from the information management server device 20.

It should be noted that, in this embodiment, the weather information acquisition source is not limited to these, and the weather information may be acquired from a server device (not illustrated) for distributing weather information via the network N.

Further, the method for specifying the weather at the location of the user is arbitrary, and for example, the communication terminal device 100 may be provided with sensors such as a thermometer, a hygrometer, and an illuminometer, and the weather may be estimated on the basis of the information obtained by the sensors, or the user may be prompted to input the current weather.

On the other hand, the irradiation amount determining part 250 compares (1) the dosed VL energy amount specified in the dosed VL energy amount calculation processing, and (2) the VL dose recommended for a user to take in one day (hereinafter referred to as "recommended dose") in order to suppress the onset and progression of myopia, and calculates the insufficiency with respect to the recommended dose in accordance with the comparison result.

Then, the irradiation amount determining part 250 subtracts the dosed VL energy amount calculated in the dosed VL energy amount calculation processing from the recommended dose, and calculates the insufficiency with respect to the recommended dose. It should be noted that, in this embodiment, 27,900 $J/m^2$ is used as the recommended dose. However, another value may be used as the recommended dose.

While it has been basically found that outdoor activity of about 14 hours per week can suppress the onset and progression of myopia (Non-Patent Document 6), further investigation by the present inventors shows that outdoor activity of about two to three hours per day can more effectively suppress the occurrence and progression of myopia.

Further, while reports also exist indicating that an effect is produced even when the outdoor activity time per day is 80 to 90 minutes, in this embodiment, on the basis of survey results of the present inventors, a method for more effectively suppressing the onset of myopia and the like is adopted by treating the energy amount of VL applied to the eyes of the user when two to three hours of outdoor activity is performed per day as the recommended dose.

Furthermore, as described above, because a VL of 22,320 $J/m^2$ is applied to the eyes of the user when outdoor activity is performed for two hours at an illuminance of 3.1 $W/m^2$, it is possible to more effectively suppress the occurrence and progression of myopia by applying a VL of 22,320 to 33,480 $J/m^2$ per day to the eyes of the user. It should be noted that the recommended dose of 27,900 $J/m^2$ used in this embodiment is the energy amount of VL applied to the eyes of the user from sunlight when a person is active for 2.5 hours in a 3.1 $W/m^2$ environment.

(Irradiation Control Part)

The irradiation control part 260 is linked with the second light-emitting element driving circuit 114, and executes VL irradiation control processing for controlling the second light-emitting element 3 and irradiating VL onto the eyes of the user on the basis of the dose insufficiency calculated by the dose insufficiency calculation processing.

Specifically, the irradiation control part 260 determines the VL illuminance irradiated from the second light-emitting element 3 and the irradiation period so as to reach the energy amount necessary to compensate for the insufficiency calculated by the dose insufficiency calculation processing, and makes the second light-emitting element 3 emit light according to the determined illuminance for the determined period at a predetermined timing.

Further, the irradiation control part 260 executes control for making the second light-emitting element 3 emit light while the line of sight of the user detected by the line-of-sight and position detecting part 240 is toward the display screen 2 side of the communication terminal device 100.

Then, the irradiation control part 260 stores the information on the irradiation timing, the illuminance, and the irradiation period in the VL irradiation history data storage part 113b.

It should be noted that, in this embodiment, the irradiation control part 260 may execute irradiation control for irradiating VL onto the user according to an arbitrary illuminance for an arbitrary period on the basis of an instruction from the user at an arbitrary timing. Further, in this case, the irradiation control part 260 stores the information related to the executed irradiation control in the VL irradiation history data storage part 113b.

(Transmission Processing Part)

The transmission processing part 270 uploads the VL irradiation history data to the information management server device 20 at a predetermined timing while linked with the network communication part 111.

Specifically, the transmission processing part 270, by uploading the VL irradiation history data in association with the user ID corresponding to the user of the device, is configured to be capable of specifying the user corresponding to the VL irradiation history data in the information management server device 20.

It should be noted that, when the transmission processing part 270 collects and manages personal data in the information management server device 20 and uses the data for advice by a doctor, a parent, or other person responsible for protection, the personal data is uploaded in association with the VL irradiation history data and a user ID.

[2.4] VL Irradiation Control Processing

Figure 16:
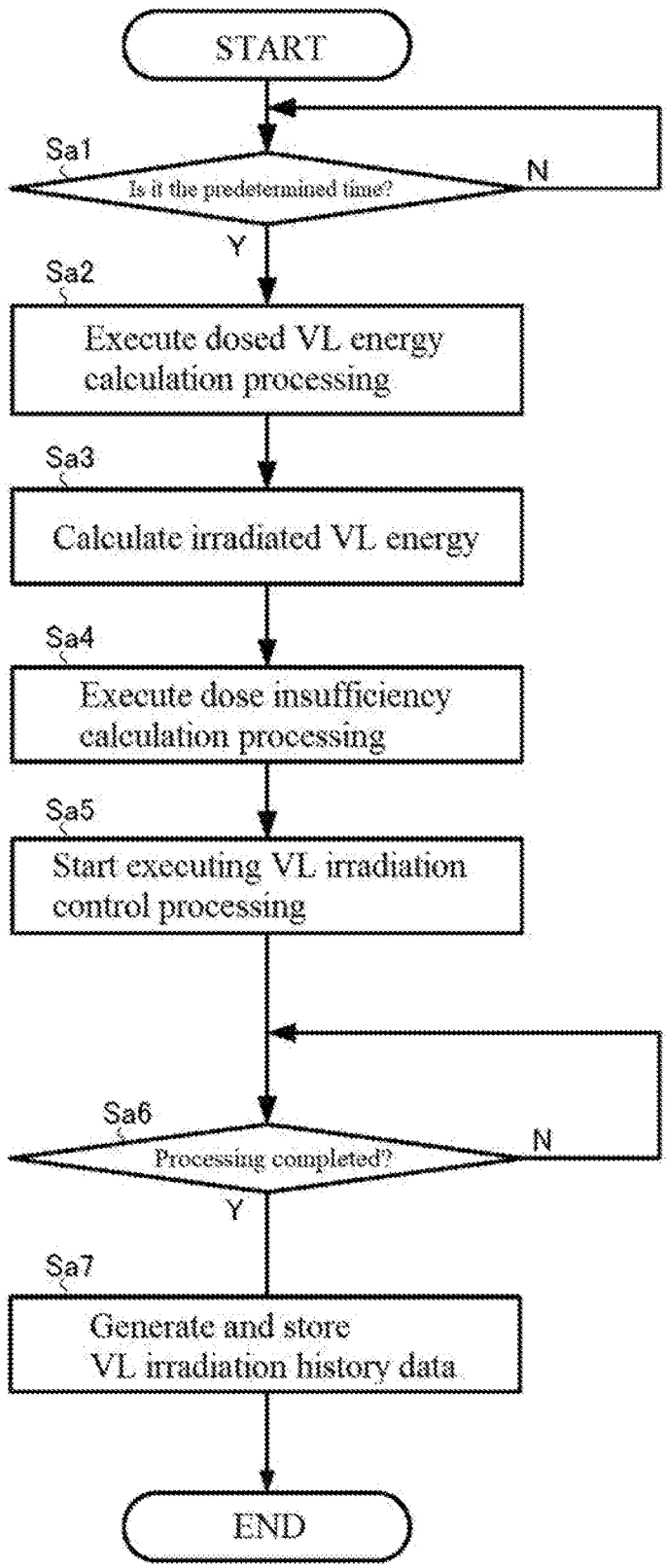
FIG. 16 is a flow chart illustrating an example of an operation of VL irradiation control processing executed in a communication terminal device of the second embodiment.

Next, the VL irradiation control processing executed in the application executing part 200 of the communication terminal device 100 of this embodiment will be described using FIG. 16. It should be noted that FIG. 16 is a flow chart illustrating the VL irradiation control processing executed in the application executing part 200 of the communication terminal device 100 of this embodiment.

In this operation, the personal data of the user is stored in the personal data storage part 113*c*.

First, when the irradiation amount determining part 250 detects a predetermined time (a predetermined time such as night before sleeping, morning upon waking, or daytime) (step Sa1), the dosed VL energy amount calculation processing (step Sa2) is executed within a predetermined past period (the past 24 hours, for example) on the basis of the personal data already stored, while linked with the data acquisition part 220.

In particular, in the dosed VL energy amount calculation processing, the irradiation amount determining part 250 calculates the outdoor location period, including area information, on the basis of the location and the indoor/outdoor status included in the personal data per predetermined time (per minute, for example).

Further, the irradiation amount determining part 250 acquires the weather information of the applicable area while linked with the network communication part 111, and VL measured value data of the applicable area and time corresponding to the weather indicated by the acquired weather information.

Then, the irradiation amount determining part 250 calculates the dosed VL energy amount within the predetermined past period of the user on the basis of the acquired VL measured value data and the calculated outdoor location period, including the area information.

Next, in a case where VL has already been irradiated onto the eyes of the user within the predetermined past period, the irradiation amount determining part 250 acquires the irradiation time and the irradiation illuminance to calculate the irradiated VL energy amount (step Sa3).

Next, the irradiation amount determining part 250 subtracts the calculated dosed VL energy amount and the irradiated VL energy amount from the recommended dose registered in advance, and executes the dose insufficiency calculation processing to calculate the VL energy amount that should be applied to the eyes of the user by the second light-emitting element 3 (step Sa4).

For example, when the irradiated VL energy amount is "3,000 J/m$^2$" and the user has been exposed to VL in an energy amount of 15,000 J/m$^2$ by outdoor activity during a predetermined period on the basis of personal data, the irradiation amount determining part 250 calculates the energy insufficiency as 9,900 J/m$^2$ (=27,900 J/m$^2$−3,000 J/m$^2$−15,000 J/m$^2$).

Next, to compensate for the insufficiency of the dose calculated in the dose insufficiency calculation processing, the irradiation control part 260 starts execution of the VL irradiation control processing (step Sa5).

Specifically, the irradiation control part 260 determines the illuminance and the irradiation period of VL and controls the second light-emitting element driving circuit 114, causing the second light-emitting element 3 to emit light by the second light-emitting element driving circuit 114 at the determined illuminance for the determined period.

Next, upon detection of the end of irradiation of VL onto the eyes of the user (step Sa6), the irradiation control part 260 generates VL irradiation history data on the basis of the light emission illuminance of the second light-emitting element 3 and the irradiation period, and stores the data in the VL irradiation history data storage part 113*b* (step Sa7). The operation then ends.

It should be noted that the transmission processing part 270 transmits (uploads) the VL irradiation history data stored in the VL irradiation history data storage part 113*b* to the information management server device 20 at a predetermined timing and the data is confirmed by the user or provided to doctors, parents, other persons responsible for protection, and the like.

As described above, the communication system S of this embodiment has the configuration mentioned above and thus is capable of applying VL in an appropriate energy amount to the eyes of the user even for a user having a short outdoor activity time. Further, the communication system S of this embodiment can specify the VL energy amount to which the user was exposed during the storage period of the life log with high precision, and calculate the dose insufficiency with respect to the recommended dose with high accuracy.

[3] Modified Examples

[3.1] Modified Example 1

While, in the above-described second embodiment, a configuration is adopted in which the second light-emitting element 3 is provided separately from the display screen 2, the illuminance and the irradiation period are determined according to the dose insufficiency, and the second light-emitting element 3 emits light at the illuminance for only the determined period, a configuration in which the first light-emitting element 6, consisting of RGB, and the second light-emitting element 3 are provided adjacent to each other in one pixel of the display screen 2 as illustrated in FIG. 6 is also possible. In this case as well, the dose insufficiency is calculated by the same processing as in FIG. 16.

Then, the irradiation control part 260 may determine the light emission illuminance and the light emission period of the second light-emitting element 3 so as to reach the dose insufficiency, and the display control part 115 may drive the display screen 2 so that VL is irradiated at the illuminance for only the determined time. It should be noted that, in this case, since one pixel consists of the four primary colors of red, green, blue, and violet (RGBV), preferably (1) the display control part 115 drives the display screen 2 while the color balance is adjusted so that the image is displayed by the four primary colors of RGBV, or (2) the first light-emitting element 6 and the second light-emitting element 3 consisting of RGB are separately and independently driven. With this configuration, it is possible to prevent loss of the color balance of the image display by the first light-emitting element 6 as a result of the light emission of the second light-emitting element 3. It should be noted that the method itself for adjusting the color balance and displaying the image by the four primary colors of RGBV is the same as in the related art.

With the adoption of this configuration, because the wavelength region of the base colors is expanded, the color rendering property is enhanced, making it possible to express colors that could not be reproduced using a conventional RGB display screen. Further, the display screen 2 may be manufactured in RGV format instead of RGB, and the image may be displayed while adjusting the color balance by RGV. In this case as well, the dose insufficiency is calculated by the same processing as in FIG. 16.

The irradiation control part 260 may determine the light emission illuminance and the light emission period of the second light-emitting element 3 (V of RGV) so as to reach the dose insufficiency, and the display control part 115 may drive the display screen 2 so that VL is output at the illuminance for only the determined period.

[3.2] Modified Example 2

While, in the above-described second embodiment, a configuration in which VL is irradiated onto the eyes of the user has been described, a configuration in which the second light-emitting element 3 illustrated in FIG. 15 is replaced with a third light-emitting element and the same processing is executed is also possible. In this case, in the third light-emitting element, a light source is manufactured using a configuration in which the third light-emitting element, which outputs light having a wavelength of about 460 nm±20 nm, is an excitation light LED, as the excitation light LED in the configuration of FIG. 5.

Based on the outdoor location period in the past 24 hours of the user, the irradiation illuminance and the irradiation period of BL is determined, and the light emission of the third light-emitting element is controlled on the basis of the determination result. In this case, the irradiance of BL in each area is measured in advance for each weather type, and BL measured value data indicating the measurement result is registered in the information management server device 20.

The irradiation amount determining part 250 calculates the dosed BL energy amount on the basis of the data of outdoor location period and the BL measured value data, and subtracts the calculated value from the recommended dose to calculate the BL dose insufficiency. Thus, the irradiation amount determining part 250 determines the illuminance and the light emission period when the third light-emitting element is to emit light on the basis of the calculated BL energy insufficiency.

The irradiation control part 260 may make the third light-emitting element emit light at the illuminance for the determined period. It should be noted that, in this case, while the third light-emitting element is driven by the second light-emitting element driving circuit 114, the second light-emitting element and the third light-emitting element are the same except for having different light emission frequencies of the excitation light LED, and thus circuit configuration of the second light-emitting element driving circuit 114 need not be significantly changed, making it possible to achieve the function by a simple adjustment only, such as adjustment of the drive voltage.

[3.3] Modified Example 3

In this embodiment, during the life log recording period, the possibility also exists that (1) the weather changes, or (2) the user travels across an area of the current location by airplane or the like, and the weather and the VL radiation amount of the current location change. In this case, in order to respond to changes in the weather during the day, the following method is adopted.

First, the personal data management part 230 divides the time band during the day into, for example, one hour time bands, such as (1) 6:01 to 7:00, (2) 7:01 to 8:00, (3) 8:01 to 9:00, (4) 9:01 to 10:00, (5) 10:01 to 11:00, (6) 11:01 to 12:00, (7) 12:01 to 13:00, (8) 13:01 to 14:00, (9) 14:01 to 15:00, (10) 15:01 to 16:00, and (11) 16:01 to 17:00, and stores the data in the personal data storage part 113c in combination with information of the time band as well.

The irradiation amount determining part 250 acquires the weather information of the user location in each time band, and VL measured value data at the user location on the basis of the weather information. Then, the irradiation amount determining part 250, on the basis of the outdoor location period in each time band and the acquired VL measured value data, calculates the energy amount of the VL to which the user was exposed in each time band. The irradiation amount determining part 250 calculates the energy amount of the VL to which the user was actually exposed during the storage period of the life log (that is, the dosed VL energy amount) by adding the energy amounts thus calculated, and calculates the dose insufficiency by subtracting the calculated dosed VL energy amount from the recommended dose.

The irradiation control part 260 makes the second light-emitting element 3 emit light in accordance with the calculation result. With this configuration, even when the weather at the user location changes during the storage period of the life log, the dose insufficiency can be accurately calculated, and VL in the amount equivalent to the insufficiency can be applied to the eyes of the user, making it possible to effectively suppress the occurrence and progression of myopia.

It should be noted that, as long as a configuration is adopted in which the daytime time band is divided into a plurality of sections with even shorter time bands, and the period located outdoors by the user and weather are specified for each time band, the dose insufficiency can be more accurately specified.

Even when the user moves during the storage period of the life log, the irradiation amount determining part 250 acquires the VL measured value data from the information management server device 20 on the basis of the location of the user for each time band as well as the weather of the corresponding time band of the location, and calculates the dosed VL energy amount on the basis of the acquired VL measured value data and the outdoor location period in the time band.

With this configuration, even when the user travels by airplane or the like during the storage period of the life log, the dose insufficiency can be accurately specified, and the second light-emitting element 3 can emit and irradiate light onto the eyes of the user in accordance with the specified result, making it possible to effectively prevent the occurrence and progression of myopia.

[3.4] Modified Example 4

While, in the above-described embodiment, an installation position of the sensor part 120 is not explicitly shown, the sensor part 120 may be provided in a main body part of the communication terminal device 100 or in a wearable terminal device. It should be noted that, because it is difficult to accurately measure the irradiance of VL in the periphery of the user when the communication terminal device 100 is put in a bag or a pocket, preferably the sensor part 120 is provided in a wearable terminal device. More preferably, in order to measure the irradiance of VL at the position of the eyes of the user, for example, the sensor part 120 is preferably provided on eyeglasses.

When the VL irradiance is measured at the position of the eyes, the dosed VL energy amount is calculated including the energy amount of the VL irradiated onto the eyes of the user, which also includes the irradiance of the VL irradiated from the display screen 2, making it possible to calculate the VL energy insufficiency with even higher precision.

[3.5] Modified Example 5

While, in the above-described second embodiment, the time band in which the VL is irradiated onto the eyes of the user by the second light-emitting element 3 is not defined, humans should actually be exposed to VL from sunlight in time bands during the day, and therefore preferably VL irradiation onto the eyes of the user by the second light-emitting element 3 is also implemented in time bands during the day in order to regulate the circadian rhythm.

In this modified example, when the VL irradiation control processing is executed after the calculation of the dose insufficiency, the irradiation control part 260 acquires the current time by the timer 119, and makes the second light-emitting element 3 to emit light when the current time is in the time band of about 5:00 to 18:30.

Normally, it is known that the human body repairs and recovers minor damage sustained in the eye over approximately 48 hours. Therefore, with regard to the VL applied to the eyes of the user as well, it is highly possible that the onset and progression of myopia can be suppressed even when VL can be not necessarily applied within 24 hours, but within the next 24 hours. For this reason, in this modified example, a configuration may be adopted in which, when the VL dose within 24 hours, which is the storage period of the life log, is insufficient and the daytime time bands have already ended, VL in an amount equivalent to the insufficiency is irradiated onto the eyes of the user in the daytime time bands for the next 24 hours.

It should be noted that, because it has been found that irradiation of VL onto the eyes of the user is cumulative in time bands of about 24 to 48 hours, VL irradiated at an interval of about 10 hours following 30 minutes of VL irradiation can suppress the onset of myopia and the like of the user in the same manner as VL irradiated onto the eyes of the user within 24 hours.

In this modified example, a VL insufficiency of a previous day is applied in the next daytime time bands. With this configuration, it is possible to irradiate VL onto the eyes of the user only in daytime time bands, regulate the circadian rhythm, and effectively suppress the occurrence and progression of myopia. It should be noted that the same holds true even for a case where BL is irradiated onto the eyes of the user.

The irradiation mode is also arbitrary and, for example, the light may be emitted in a pulsating manner, or continually by the second light-emitting element 3 at the illuminance determined in the VL irradiation control processing.

According to the present invention described above, it is possible to irradiate light having a specific wavelength, which is missing in a modern lifestyle, toward the eyes of the user, and thus promote a favorable effect of eye exposure to light such as, for example, suppressing the onset and the progression of myopia. Furthermore, it is possible to achieve effects such as regulation, adjustment, prevention, and treatment in relation to the body and mind of the user.

DESCRIPTIONS OF REFERENCE NUMERALS

1 Display device, display system (smartphone or personal computer)
2 Display screen
3 Second light-emitting element (light-emitting element for light having a specific wavelength)
4 Frame
5 Accessory (light-emitting element)
6 First light-emitting element (light-emitting element for image display)
7 Irradiated light
8 Sensor
10 Control unit
11 Area of second light-emitting element and the like
12 Area of eyes
13 Area of display screen
20 Information management server device
30 GPS satellite
50 User
51 Eye
111 Network communication part
112 I/O interface part
113 Storage part
113a Application storage part
113b VL irradiation history data storage part
113c Personal data storage part
113d RAM
114 Second light-emitting element driving circuit
115 Display control part
116 Management control part
117 Camera part
118 Operation part
119 Timer
120 Sensor
200 Application executing part
210 Location specifying part
220 Data acquisition part
230 Personal data management part
240 Line-of-Sight detecting part
250 Irradiation amount determining part
260 Irradiation control part
270 Transmission processing part

What is claimed is:

1. A display system comprising:
a device including a light-emitting element that emits toward a user display light used for image display, and first special light within a wavelength range of 360 nm to 400 nm, inclusive, that suppresses the onset and the progression of myopia of the user;
acquisition means for acquiring personal data indicating a given activity of the user within a predetermined past period; and
a control unit that controls irradiation of the first special light on the basis of the acquired personal data when an image is displayed by the display light, wherein
the control unit specifies a period when the user is outdoors in a time band during the day for the predetermined period as an outdoor location period on the basis of the acquired personal data, acquires (1) weather information indicating the weather in the time band during the day and (2) an average value of spectral irradiance of the first special light for each weather type observed outdoors in the time band during the day, calculates an energy amount of the first special light included in sunlight to which the user is exposed during outdoor activity in the time band during the day as a dosed energy amount on the basis of the specified outdoor location period and the acquired weather information and average value, and irradiates the first special light while determining an illuminance and an irradiation period of the first special light on the basis of the calculated dosed energy amount and an irradiated energy amount of the first special light acquired in advance that exhibits an effect of suppressing the onset and the progression of myopia.

2. The display system according to claim 1, wherein the first special light is emitted from an integrated light-emitting element that emits the light along with the display light, or emitted from a separated light-emitting element that emits the light separately from the display light.

3. The display system according to claim 1, wherein the light-emitting element comprises a first light-emitting element that emits the display light and a second light-emitting element that emits the first special light, the second light-emitting element being (A) provided to a peripheral frame of a display screen of the device, (B) provided in the display screen, or (C) provided as an accessory of the device.

4. The display system according to claim 1, further comprising:
detection means for detecting at least one of (1) a position of an eye of the user, (2) an open/closed state of an eyelid, (3) a distance to the eye, and (4) a line-of-sight direction of the user, wherein
the control unit controls irradiation of the first special light to the eye of the user on the basis of at least one of the position of the eye, the open/closed state of the eyelid, the distance to the eye, and the line-of-sight direction of the user detected by the detection means.

5. The display system according to claim 4, wherein the control unit irradiates the first special light toward the eyes of the user when the line of sight of the user is determined to be toward a display screen displaying the image on the basis of the detected line-of-sight direction.

6. The display system according to claim 1, wherein the acquisition means, in addition to acquiring the personal data, measures a state of light at a position of the eye of the user in the environment where the user is placed, and
the control unit determines an illuminance and an irradiation period of the first special light in accordance with the state of light acquired at a position of the eye of the user, and adjusts output of the display light in accordance with the first special light.

7. The display system according to claim 1, wherein the acquisition means, in addition to the personal data, acquires irradiation history data related to an irradiation history of the first special light irradiated by the light-emitting element in the predetermined period, and
the control unit specifies an energy amount of the first special light irradiated by the light-emitting element as an irradiated energy amount on the basis of the acquired irradiation history data, and determines an illuminance and an irradiation period of the first special light on the basis of (a) the specified irradiated energy amount, (b) the calculated dosed energy amount, and (c) the energy amount acquired in advance that exhibits the effect of suppressing the onset and the progression of myopia.

8. The display system according to claim 7, further comprising:
management means for storing the acquired irradiation history data in first storage means so as to allow use in a predetermined activity of the user, wherein
the acquisition means acquires data including data related to at least one or more control items of an irradiation time, an irradiation period, and an irradiance of the first special light as the irradiation history data.

9. The display system according to claim 8, wherein the management means acquires measurement data indicating a measurement result of the first special light measured at a position of the eye of the user, stores the acquired irradiation history data and the measurement data in association with a time in the first storage means, and supplies the stored irradiation history data and measurement data to an external device.

10. The display system according to claim 1, wherein the control unit irradiates the first special light in the time band during the day.

11. The display system according to claim 1, wherein when the weather changes in a time band during the day corresponding to the personal data, the control unit specifies the outdoor location period of the user under each weather type, calculates the dosed energy amount on the basis of the specified outdoor location period, the weather information, and the average value, and determines an illuminance and an irradiation period of the first special light on the basis of the calculated dosed energy amount and the irradiated energy amount of the first special light acquired in advance that exhibits the effect of suppressing the onset and the progression of myopia.

12. The display system according to claim 1, wherein when the user moves to an area where the weather or an average value of an irradiance of the first special light is different in a time band during the day corresponding to the personal data, the control unit specifies the outdoor location period of each located area of the user, calculates the dosed energy amount on the basis of the outdoor location period of each specified area, the weather information, and the average value, and determines an illuminance and an irradiation period of the first special light on the basis of the calculated dosed energy amount and the irradiated energy amount of the first special light acquired in advance that exhibits the effect of suppressing the onset and the progression of myopia.

13. The display system according to claim 1, wherein an irradiance of the first special light is 10 $W/m^2$ or less.

14. The display system according to claim 1, further comprising:
a light-emitting element that is provided in the device and irradiates a second special light within a wavelength range of 460 nm±20 nm toward the user, the display system controlling irradiation of the second special light from the light-emitting element.

15. The display system according to claim 14, wherein the light-emitting element that emits the second special light is included in the light-emitting element that emit the display light.

16. The display system according to claim 14, wherein an irradiance of the second special light is 1 $W/m^2$ or less.

17. The display system according to claim 1, wherein the control unit restricts, of the light being irradiated on the user, at least one or both of light within a range of 435 nm±10 nm and light within a range of 505 nm±10 nm.

18. An electronic device comprising the display system described in claim 1.

19. A lighting system comprising:
a light source configured by a light-emitting element that irradiates a first special light that suppresses the onset and the progression of myopia of a user and is within a wavelength range of 360 nm to 400 nm, inclusive, and a fluorescent material that covers a periphery of the light-emitting element;

acquisition means for acquiring personal data indicating data of a given activity of the user within a predetermined past period; and a control unit that controls emission of the first special light by the light source on the basis of the acquired personal data when the fluorescent material emits light, wherein the control unit specifies a period when the user is outdoors in a time band during the day for the predetermined period as an outdoor location period on the basis of the acquired personal data, acquires (1) weather information indicating the weather in the time band during the day and (2) an average value of spectral irradiance of the first special light for each weather type observed outdoors in the time band during the day, calculates an energy amount of the first special light included in sunlight to which the user is exposed during outdoor activity in the time band during the day as a dosed energy amount on the basis of the specified outdoor location period and the acquired weather information and average value, and irradiates the first special light while determining an illuminance and an irradiation period of the first special light on the basis of the calculated dosed energy amount and an irradiated energy amount of the first special light acquired in advance that exhibits an effect of suppressing the onset and the progression of myopia.

20. A display system comprising:

a display element that emits display light used for image display toward a user;

a light-emitting element that emits toward the user first special light within a wavelength range of 360 nm to 400 nm, inclusive, that suppresses the onset and the progression of myopia of the user; and a control unit that controls at least irradiation of the first special light emitted by the light-emitting element, wherein the control unit determines an illuminance and an irradiation period on the basis of an energy amount of the first special light required to exhibit an effect of suppressing the onset and the progression of myopia, the energy amount reliably recovering effects that occur in the eyes of the user by irradiation of the first special light within a predetermined period, controls the light-emitting element on the basis of the determined illuminance and an irradiation period, and irradiates the first special light on the user.

* * * * *